(12) United States Patent
Stone et al.

(10) Patent No.: US 10,456,119 B2
(45) Date of Patent: Oct. 29, 2019

(54) BIOPSY ACTUATOR ASSEMBLY

(71) Applicant: 3DBiopsy, Inc., Aurora, CO (US)

(72) Inventors: Nelson N. Stone, Vail, CO (US);
Timothy Patrick Crowley, Arvada, CO (US)

(73) Assignee: 3DBiopsy, Inc., Aurora, CO (US)

( * ) Notice: Subject to any disclaimer, the term of this patent is extended or adjusted under 35 U.S.C. 154(b) by 91 days.

(21) Appl. No.: 15/728,968

(22) Filed: Oct. 10, 2017

(65) Prior Publication Data
US 2018/0098757 A1    Apr. 12, 2018

Related U.S. Application Data

(60) Provisional application No. 62/406,292, filed on Oct. 10, 2016.

(51) Int. Cl.
*A61B 5/00* (2006.01)
*A61B 10/02* (2006.01)

(52) U.S. Cl.
CPC ...... *A61B 10/0266* (2013.01); *A61B 10/0275* (2013.01); *A61B 2010/0208* (2013.01)

(58) Field of Classification Search
CPC . A61B 10/02; A61B 10/0233; A61B 10/0266; A61B 10/0275; A61B 2010/0208
See application file for complete search history.

(56) References Cited

U.S. PATENT DOCUMENTS

| | | | |
|---|---|---|---|
| 5,335,672 A | 8/1994 | Bennett | |
| 5,546,957 A | 8/1996 | Heske | |
| 5,570,699 A * | 11/1996 | Kass | A61B 10/0275 600/567 |
| 5,752,923 A | 5/1998 | Terwilliger | |
| 5,916,175 A | 6/1999 | Bauer | |
| 6,106,484 A | 8/2000 | Terwilliger | |
| 6,592,530 B1 * | 7/2003 | Farhadi | A61B 10/0275 600/564 |
| 6,749,576 B2 | 6/2004 | Bauer | |
| 8,016,772 B2 | 9/2011 | Heske et al. | |
| 8,197,419 B2 | 6/2012 | Field et al. | |
| 8,343,072 B2 | 1/2013 | Bacon et al. | |
| 8,500,654 B2 | 8/2013 | Goldenberg | |
| 8,506,504 B2 | 8/2013 | Field et al. | |
| 9,149,260 B2 * | 10/2015 | Stone | A61B 90/39 |
| 9,289,192 B2 | 3/2016 | Stone | |

(Continued)

*Primary Examiner* — Max F Hindenburg
(74) *Attorney, Agent, or Firm* — Spencer Fane LLP

(57) ABSTRACT

A biopsy needle actuator includes an adjustable stop plate setting the distance a needle and cannula move when the actuator is fired, a shot counter tracking the number of shots taken with the actuator during a biopsy procedure, and a lifecycle indicator tracking the cumulative number of shots of the actuator during a recommended service life. A threaded rod sets the throw distance of the needle and cannula allowing the actuator to excise a biopsy tissue specimen of between 20 mm and 60 mm. A number wheel in the shot counter is moved upon firing of a needle carrier. The lifecycle indicator registers arming of the actuator and indicates when the mechanical components of the actuator need servicing. A biopsy needle within a cannula is mounted in the actuator where by the core bed of the needle is orientated downward when in use aiding in extraction of the tissue sample.

33 Claims, 33 Drawing Sheets

(56) References Cited

U.S. PATENT DOCUMENTS

| | | |
|---|---|---|
| 9,398,922 B2 * | 7/2016 | Parihar .............. A61B 17/3403 |
| 10,064,608 B2 * | 9/2018 | Goldenberg ....... A61B 10/0275 |
| 2003/0163152 A1 | 8/2003 | Weilandt |
| 2004/0249307 A1 | 12/2004 | Thompson et al. |
| 2005/0159676 A1 | 7/2005 | Taylor et al. |
| 2010/0160826 A1 | 6/2010 | Parihar |
| 2011/0105946 A1 | 5/2011 | Sorensen |
| 2012/0179065 A1 | 7/2012 | Ferree et al. |
| 2012/0215130 A1 | 8/2012 | Field et al. |
| 2012/0253230 A1 | 10/2012 | Williams et al. |
| 2013/0006144 A1 | 1/2013 | Clancy et al. |
| 2013/0102925 A1 | 4/2013 | McGhie |

* cited by examiner

BIOPSY ACTUATOR ASSEMBLY

CROSS-REFERENCE TO RELATED APPLICATIONS

This application claims priority in U.S. Patent Application Ser. No. 62/406,292, filed Oct. 10, 2016, the contents of which are hereby incorporated by reference.

BACKGROUND

1. Field of the Invention

Biopsy instruments, components thereof, and methods of using biopsy instruments.

2. Background

Biopsy procedures involve precision instruments used to remove small tissue samples. Multiple tissue samples are often gathered during a time consuming procedure. Preferably, the numerous tissue samples should be quickly obtained and accurately tracked. In addition, the biopsy instruments should be serviced or replaced prior to failure.

SUMMARY

The needle actuator includes a cannula carrier that moves on a cannula carrier guide shaft. A needle carrier moving on a needle carrier guide shaft is adjacent the cannula carrier and shaft. A biopsy needle is operably connected to the needle carrier, and the biopsy needle moves within a cannula operably connected to the cannula carrier.

The carriers move between an armed position and a fired position. An adjustable stop plate determines the fired position of the carriers. The carriers are moved to an armed position by moving the carriers away from the stop plate and compressing springs that bias the needle carrier and cannula carrier toward the stop plate. Pulling a loading lever away from the housing engages a lever carrier with the carriers moving the carriers from a fired position to an armed position. Moving the carriers into an armed position compresses springs biasing the carriers toward the stop plate.

The distance between the front of the carriers and the stop plate is adjusted by rotating a threaded rod, positioning the stop plate between about 20 millimeters to about 60 millimeters from the front of the carriers, thus setting the desired thrown length of the biopsy needle, and determining the length of the resulting biopsy specimen. Tabs extending from the stop plate index against numbers formed in the housing allowing a user to see the resulting throw length of the needles from the exterior of the actuator. A fin extending from the rear of each carrier is visible within a window in the housing providing an indication to a user when each carrier is in an armed position.

Fire levers pivotally connected to the housing retain the carriers in the armed position. Depressing a fire button disengages the fire levers from the carriers allowing the carriers to move from the armed position to the fired position. A safety switch prevents movement of the fire button.

Contact of the needle carrier with the stop plate moves a cannula trigger that disengages a tertiary fire lever preventing movement of the cannula carrier from the armed position to the fired position.

A biopsy needle actuator employing an event counter includes number wheels actuated upon the firing of the actuator. An adjustment member allows adjustment of the number wheels. An advancement member engages a first number wheel to rotate the wheel. The advancement member engages the first number wheel upon firing the actuator as a guide biases the advancement member into engagement with the wheel. Upon completion of the firing sequence the advancement member disengages from the first number wheel and returns to a first position. The number displayed by the event counter can be correlated with a guide, such as a written document or a computer program outlining a series of steps in a procedure, and a biopsy specimen carrier system to ensure the user is taking the correct sample, and that the sample is associated with a biopsy specimen carrier. The event counter may be enclosed within a housing, and the housing may be releasably attached to the actuator by tabs.

A user can deploy two or more actuators with event counters to expedite a biopsy procedure. The number wheels can be adjusted by a user to stagger the numbers displayed on the actuators to correlate with a sequence of biopsies.

A lifecycle indicator can be used with a biopsy needle actuator to provide a visual indication to a user that the actuator has performed a specified number of mechanical movements and has reached the end of its recommended useful life and should be serviced or replaced to ensure safe and effective operation.

The biopsy needle actuator can be used whereby the orientation of the biopsy needle core bed is downward when the tissue specimen is excised and the specimen is removed from the core bed thereby facilitating transfer of the specimen to a biopsy specimen carrier.

BRIEF DESCRIPTION OF THE DRAWINGS

The present disclosed subject matter is described herein with reference to the following drawing figures, with greater emphasis being placed on clarity rather than scale.

DETAILED DESCRIPTION

Figure 1:
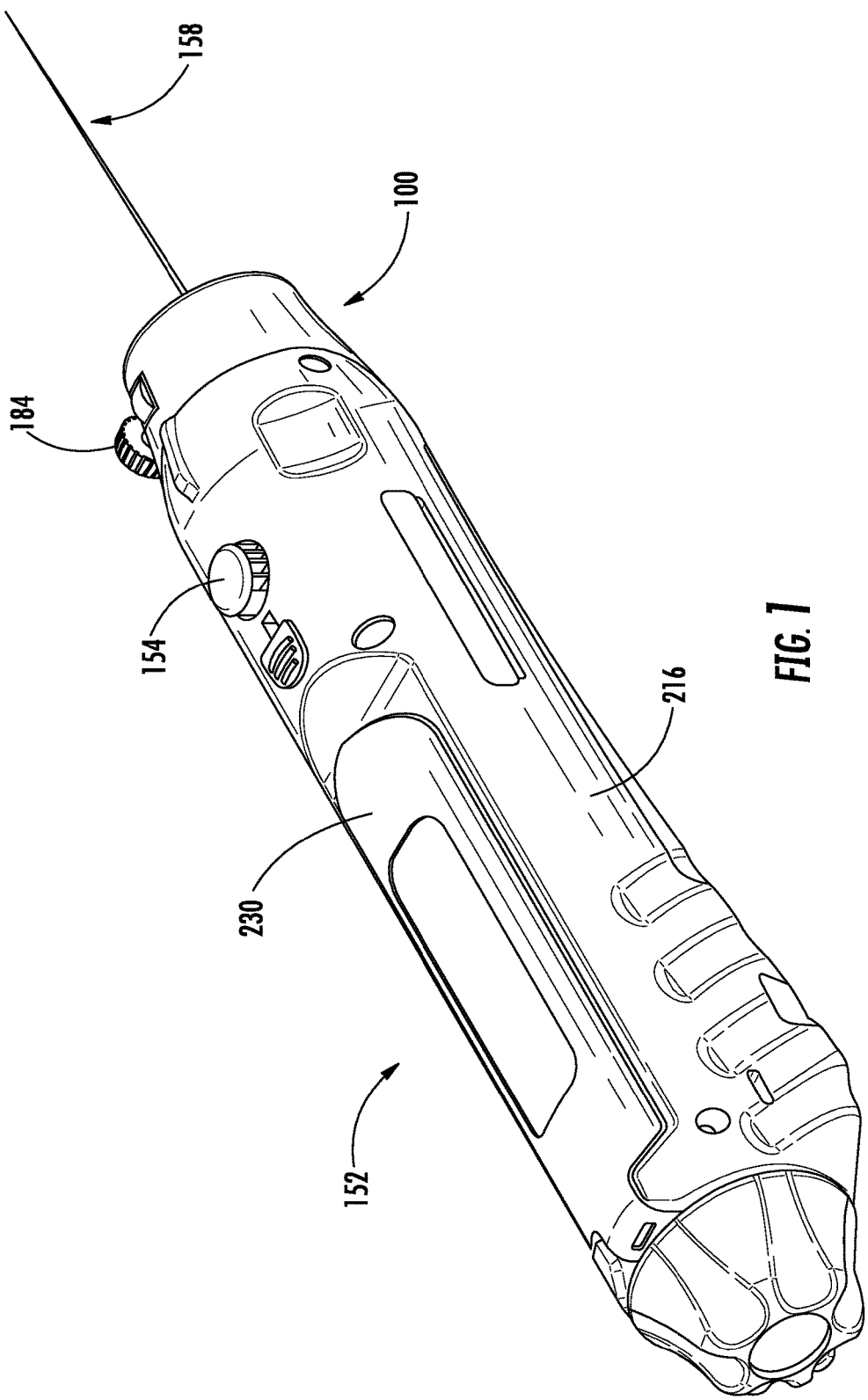
FIG. 1 is an isometric view from above of the rear of an assembly of a biopsy needle actuator with an event counter and needle assembly mounted thereto embodying aspects of the disclosed subject matter.
Figure 2:
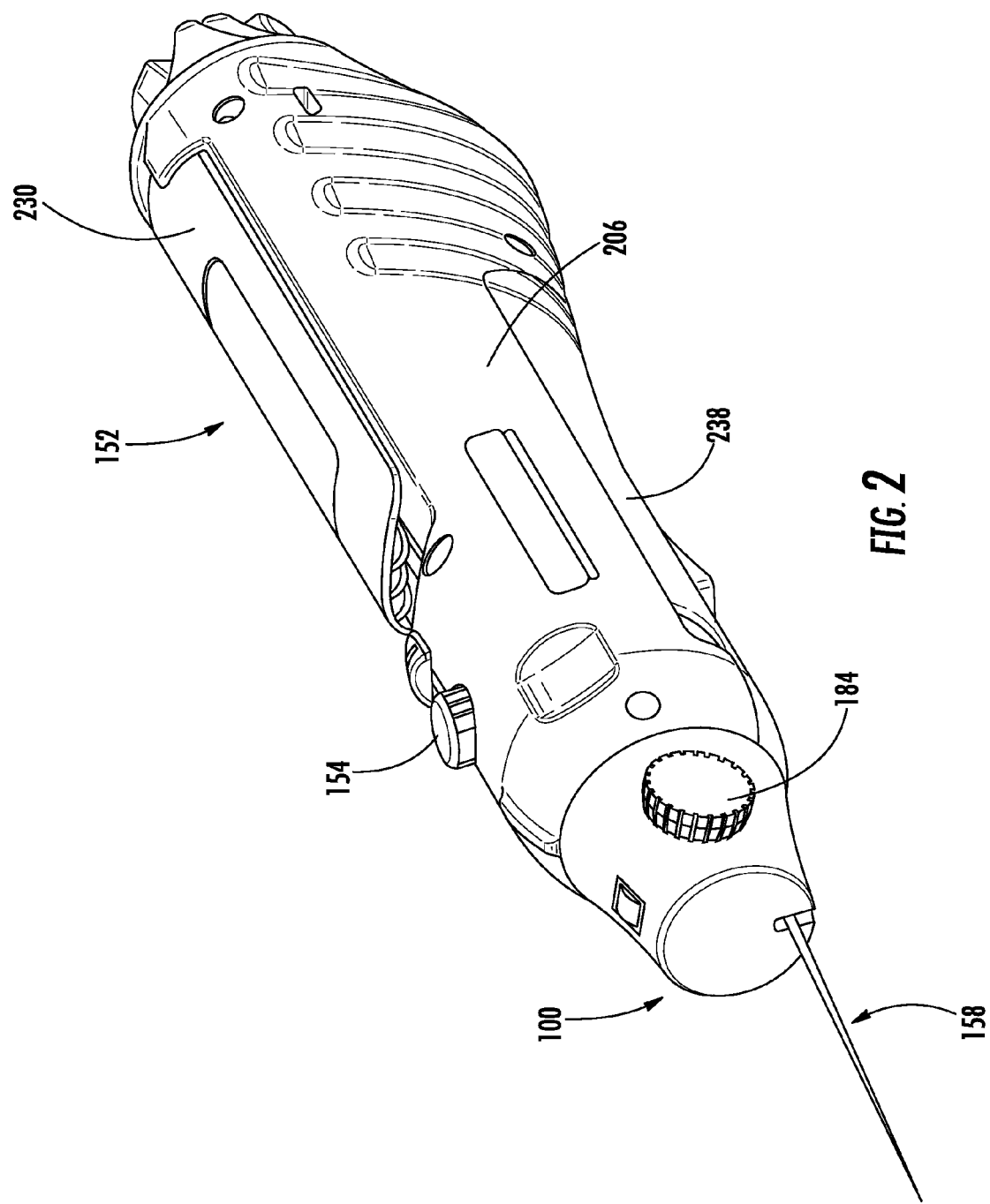
FIG. 2 is an isometric view from below of the front of an assembly of a biopsy needle actuator with an event counter and needle assembly mounted thereto embodying aspects of the disclosed subject matter.
Figure 3:
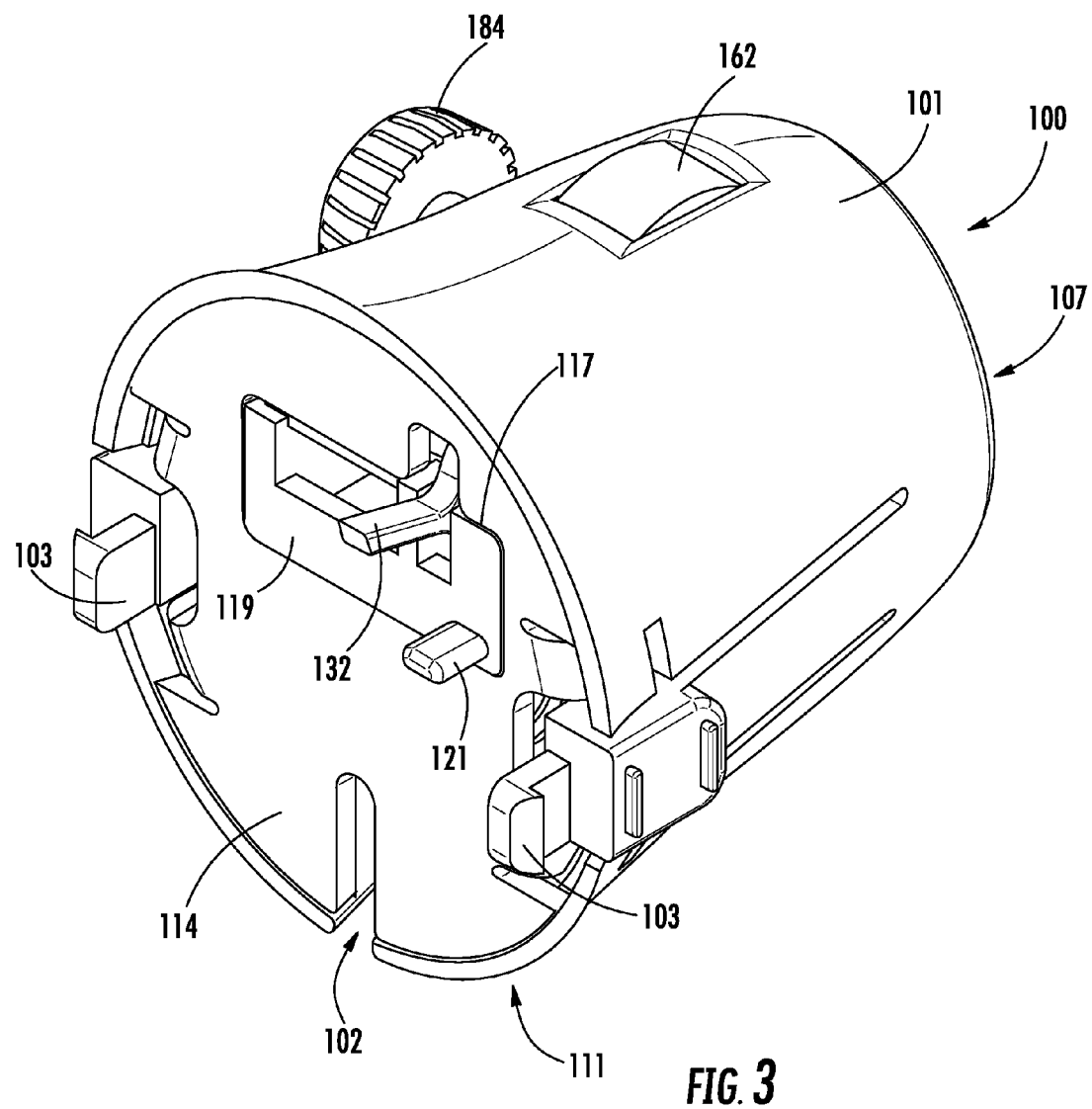
FIG. 3 is an isometric view from above of the rear of an event counter assembly within a housing embodying aspects of the disclosed subject matter.
Figure 4:
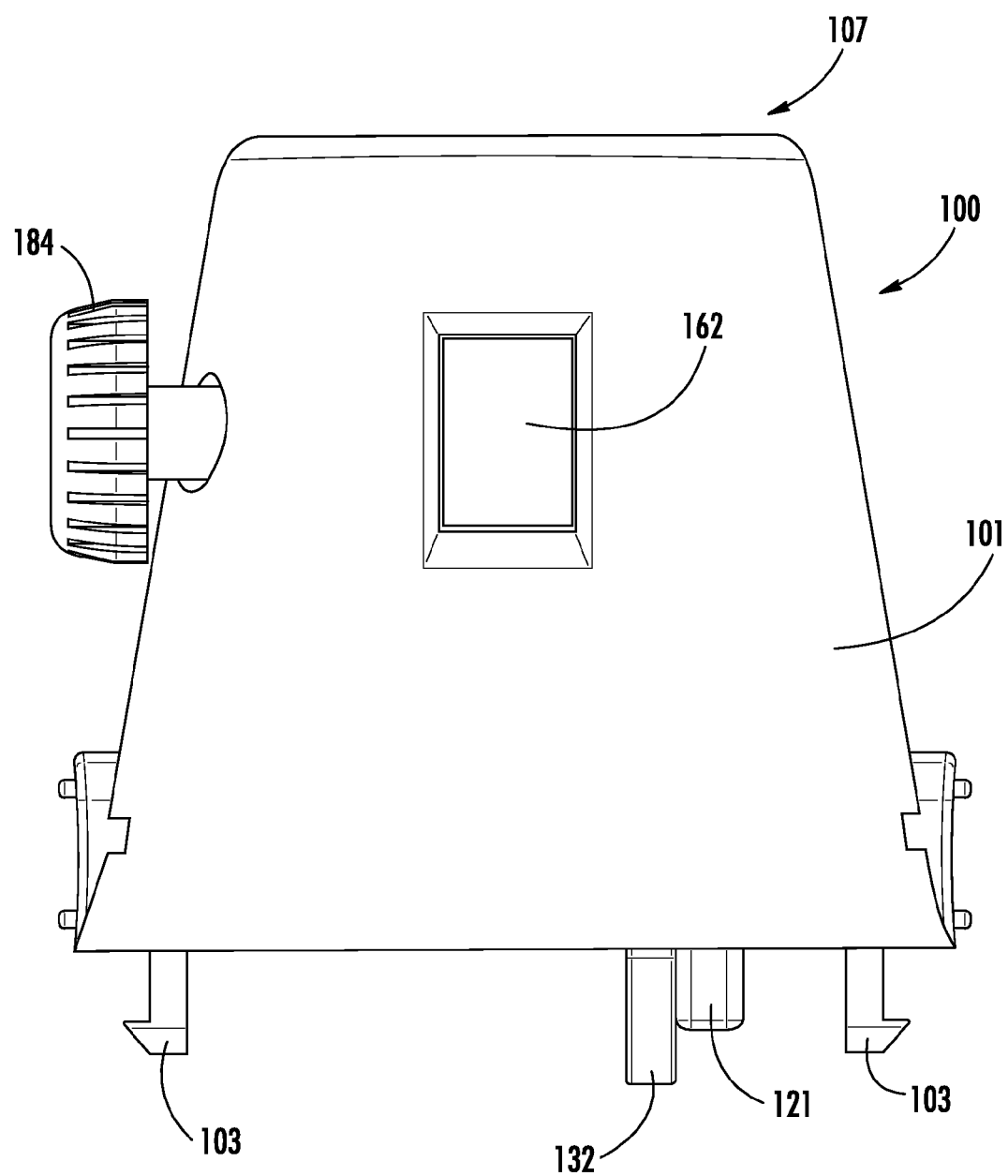
FIG. 4 is a top plan view of an embodiment of the event counter assembly of FIG. 3.
Figure 5:
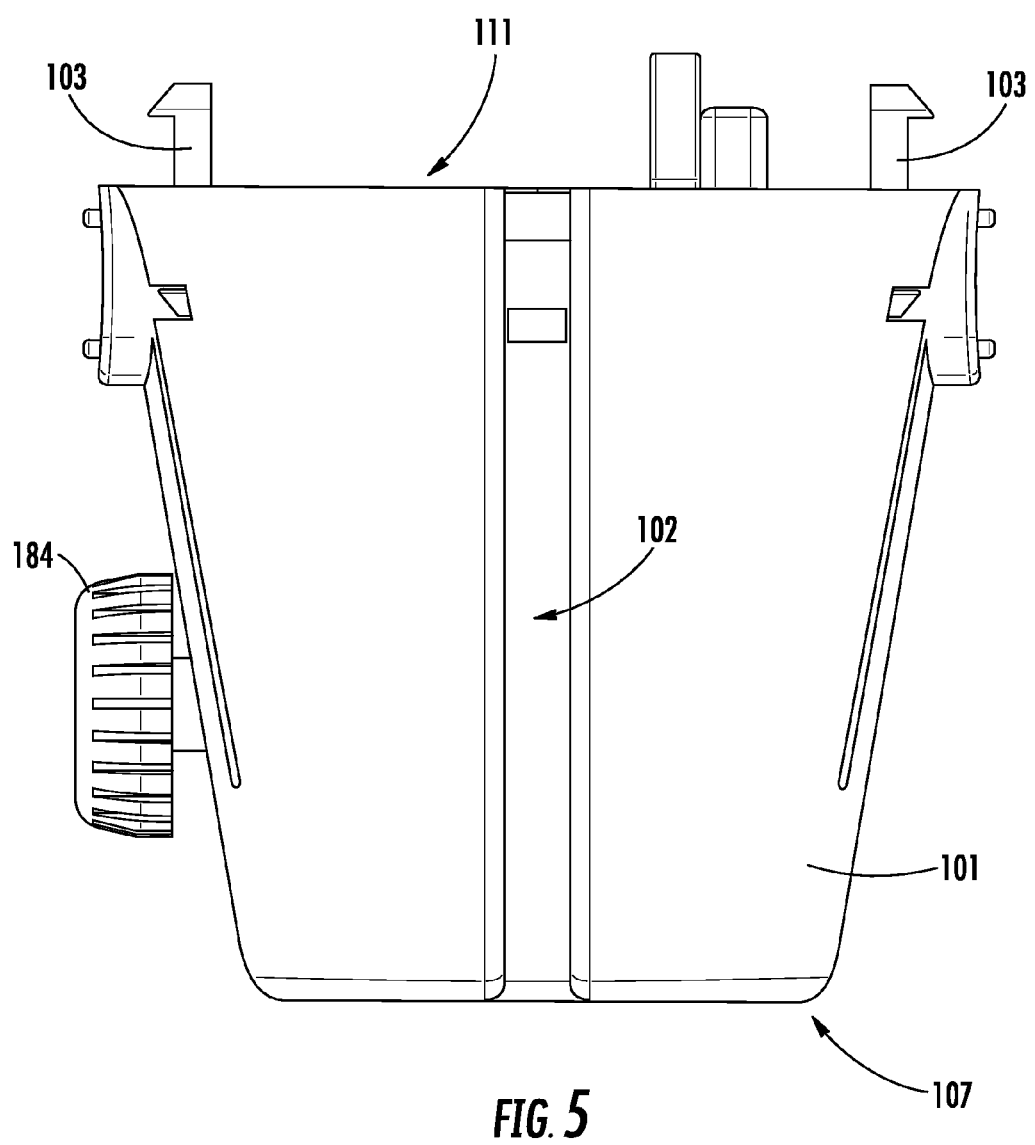
FIG. 5 is a bottom plan view of an embodiment of the event counter assembly of FIG. 3.
Figure 6:
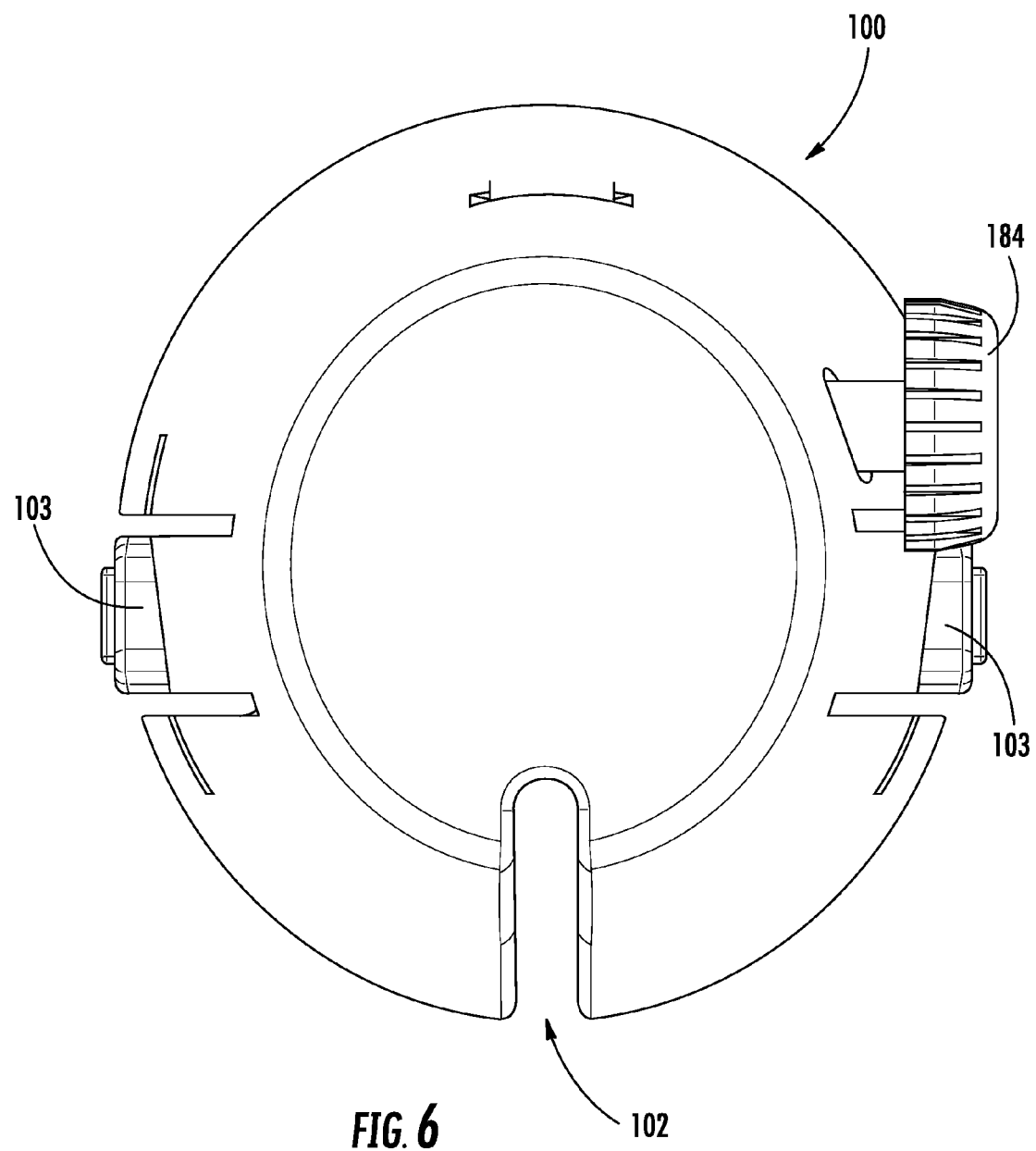
FIG. 6 is a front elevation view of an embodiment of the event counter assembly of FIG. 3.
Figure 7:
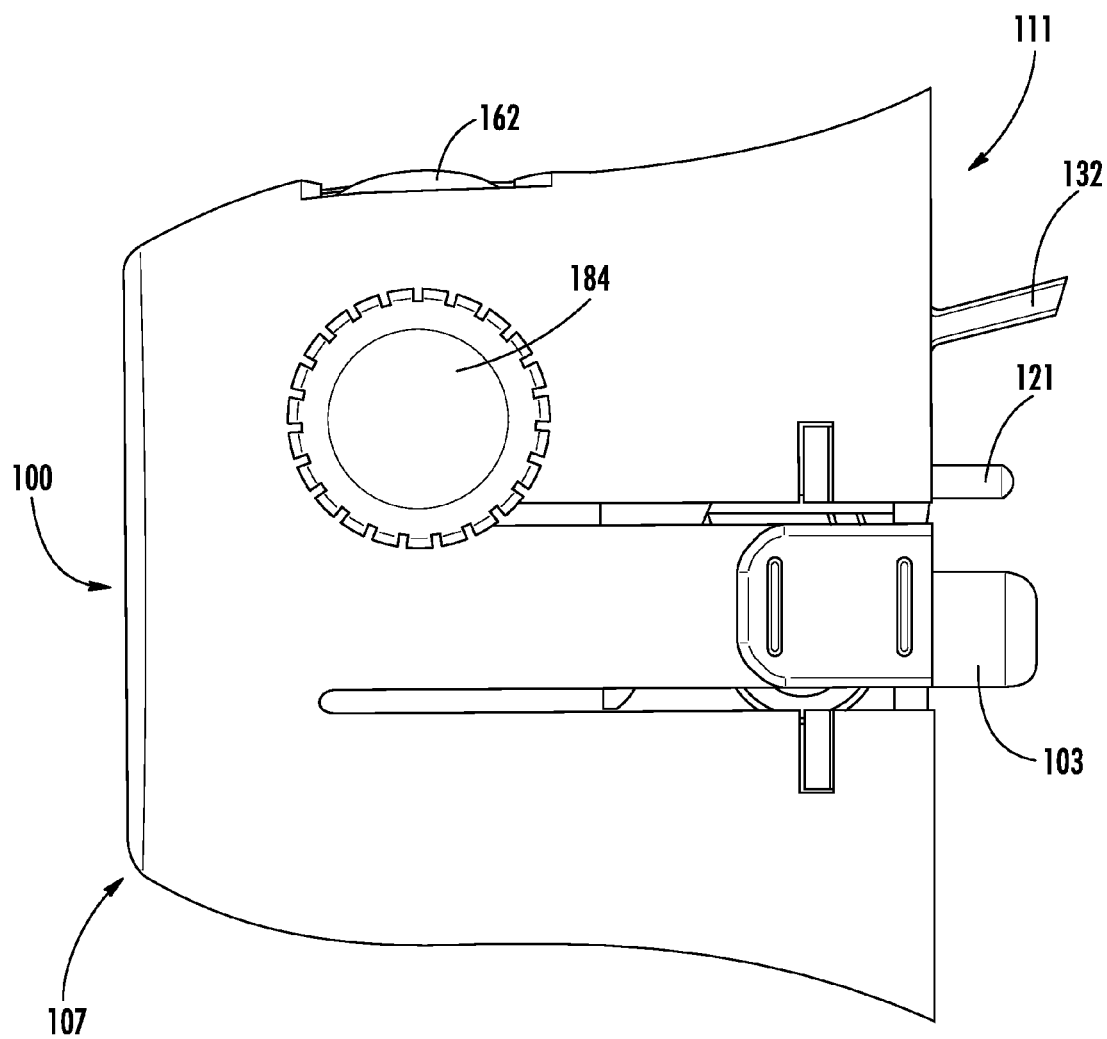
FIG. 7 is a left elevation view of an embodiment of the event counter assembly of FIG. 3.

Certain terminology will be used in the following description for convenience in reference only and will not be limiting. For example, up, down, top, bottom, front, back, rear, right, left, forward, rearward, upward, and downward refer to the disclosed subject matter as orientated in the view being referred to, or in reference to such terminology designating the characteristics of an assembly as described in this description. Such terminology will include the words specifically mentioned, derivatives thereof, and words of similar meaning. Referring to FIGS. 1-2, a biopsy needle actuator 152, also called a biopsy gun, with an event counter 100 for taking tissue samples with a biopsy needle assembly 158 is shown.

Referring to FIGS. 3-12, an event counter 100, for a biopsy needle actuator 152 is disclosed and described. The event counter 100 provides information to a user to correlate with the next event or procedure involving the biopsy instrument. The information includes a number, or alphanumeric numbers displayed to a user. The information can be correlated to a sequence of steps in a procedure, such as a medical procedure involving the biopsy needle actuator 152, where the steps of the procedure are correlated with a guide (such as a written document or a computer program outlining a series of steps in a procedure), and a biopsy specimen carrier system to ensure the user is taking the designated sample from the correct location in the target tissue of a patient.

In an embodiment, the event counter 100 includes a counter assembly operably connected to the biopsy needle actuator 152. The counter assembly registers movement of components of the actuator 152 that results in the firing of the components of the biopsy needle assembly 158, including registering movement of the firing button 154. An embodiment of the event counter 100 includes a counter assembly operably connected to the biopsy needle actuator 152 registering movement of components of the actuator 152 resulting in the charging or force loading of the biopsy needle assembly 158 prior to firing the needle assembly 158 into a target tissue 186. In an embodiment, the counter assembly is attached to a biopsy needle actuator 152 when in use, and after use, the event counter 100 is removed from the biopsy needle actuator 152 and cleaned for reuse or discarded. In an embodiment, the biopsy needle assembly 158 includes a mandrel or needle 188 with a core bed 190 at a proximal end forming a cavity 191, and a cannula 193 within which the needle 188 travels.

The counter assembly includes one or more numbers wheels that rotate displaying numbers indicating the number of times the actuator has been fired. In an embodiment, the counter assembly includes, in part, a first number wheel 104 and second number wheel 106, each numbered sequentially from zero through nine, that rotate with the numbers visible to a user through a window 162 or lens in a housing 101 or body of the event counter 100. In an embodiment, the window 162 magnifies the digits on the number wheels 104, 106, and enlarges the field of view of the numbers for the user. In an embodiment, the number wheels 104, 106 are arranged together within a mount 108. The mount 108 forms a first side 110 and a second side 112 joined by a rear portion 119 and an opposite front portion. A number wheel pivot pin 135 extends between the first side 110 and second side 112, and rotates within an aperture in each side.

An adjustment member 184 is connected to the number wheel pivot pin 135. The first number wheel 104 is located between the first side 110 of the mount 108 and the second number wheel 106. The first number wheel 104 registers digits zero to nine, rotating one digit upon each firing of an actuator 152 connected thereto. The first number wheel 104 includes a central opening with a key 123 for engaging a keyway 136 in the number wheel pivot pin 135, whereby rotation of the adjustment member 184 rotates the first number wheel 104 allowing a user to rotate the first number wheel 104 to increase or decrease the number visible in a window 162 to zero out the display or to pre-set the numbers during use of the actuator 152. In an embodiment, the adjustment member is a rotatable wheel operably connected to the first number wheel 104. For example, a user may employ two or more biopsy needle actuators 152 each with counter assemblies allowing a user to proceed through a biopsy procedure more quickly. The event counter 100 on each actuator 152 can be pre-set whereby the first actuator 152 displays a number corresponding to a first step in a sequence of events, and the second actuator 152 displays a number corresponding to a second step in a sequence of events. After the user performs a procedure using the first actuator 152, the user performs the next step in the procedure using the second actuator 152 while the number displayed by the first actuator is adjusted to display a number corresponding to a third step in the sequence of events. Any number of actuators 152 can be used in the sequence described above. In addition, the event counter 100 can be modified whereby actuation of the firing mechanism 156 advances the numerical number displayed by the event counter 100 one or more numbers to accommodate the number of actuators 152 used during a procedure. For example, when four actuators 152 are used during a procedure, the event counter 100 on each actuator 152 can be set to advance the number displayed by four. In such a scenario, the first actuator 152 used in the procedure could be set whereby the number displayed by the event counter 100 advances by four after each firing thereby avoiding a need to manually adjust the number shown by the event counter 100, allowing the first actuator 152 to be used for the fourth step in the procedure, and displaying the current number for the fourth step in the procedure.

In another embodiment, two needle actuators 152 with counter assemblies 100 are used where the first actuator 152 is designated as "A," and the second actuator 152 is designated as "B," and the procedure begins by first using actuator A, with the actuator event counter 100 displaying "01" to take a first biopsy "A01," followed by using actuator B, with the event counter 100 displaying "01" to take a second biopsy "B01," followed by using actuator A, with the event counter 100 displaying "02" to take a third biopsy "A02," and so forth until the desired number of biopsies are taken during the procedure.

The second number wheel 106 is between the second side 112 and the first number wheel 104, and the second number wheel 106 registers the tens of firing of the actuator 152. The second number wheel 106 includes a central opening allowing the second number wheel 106 to rotate about the number wheel pivot pin 135. The second number wheel 106 advances one digit when the first number wheel 104 moves between digit 9 and digit 0. Accordingly, first and second number wheels 104, 106 together sequentially display numbers 00 through 99.

Figure 8:
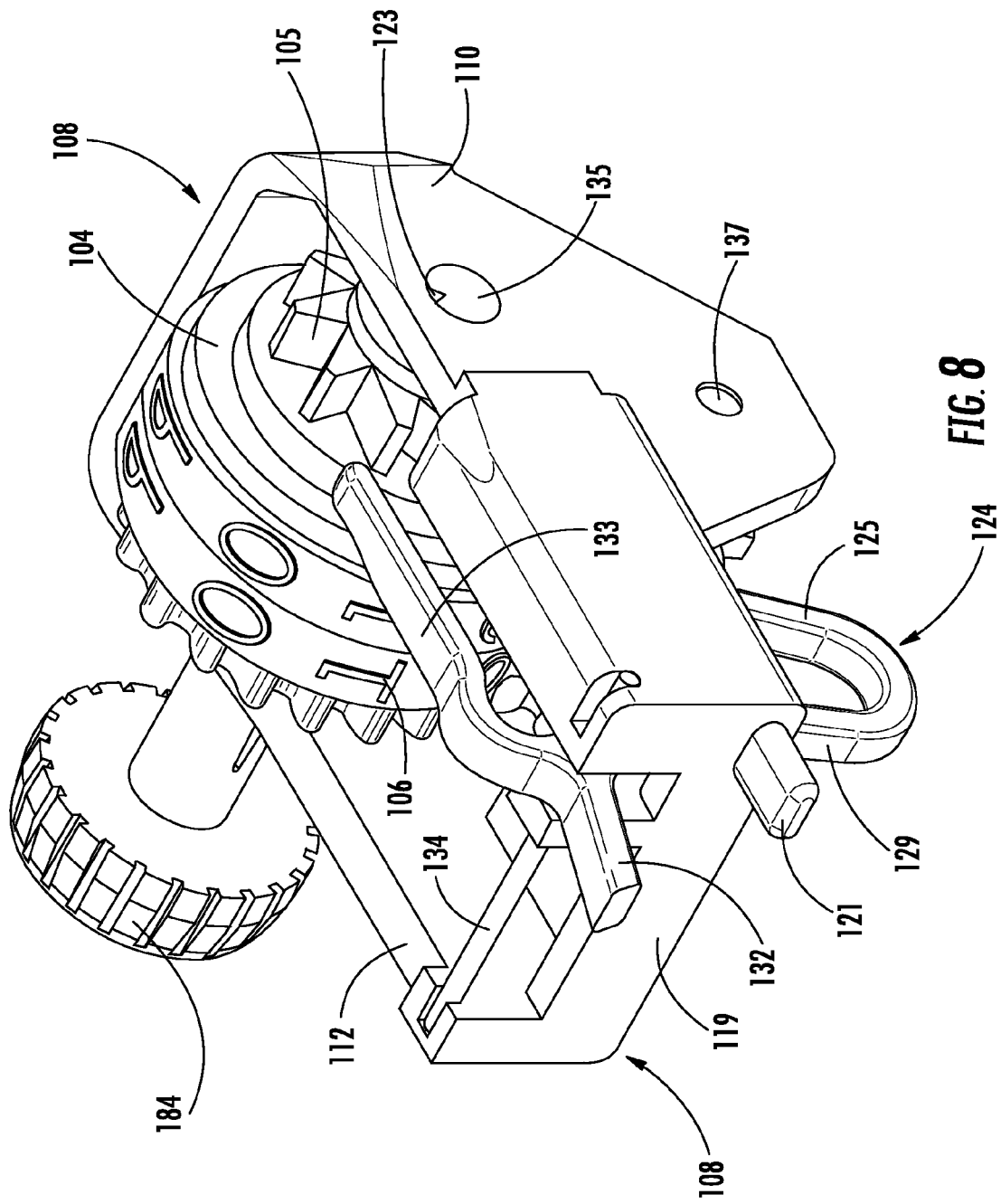
FIG. 8 is an isometric view from above of the rear of an event counter assembly embodying aspects of the disclosed subject matter.
Figure 9:
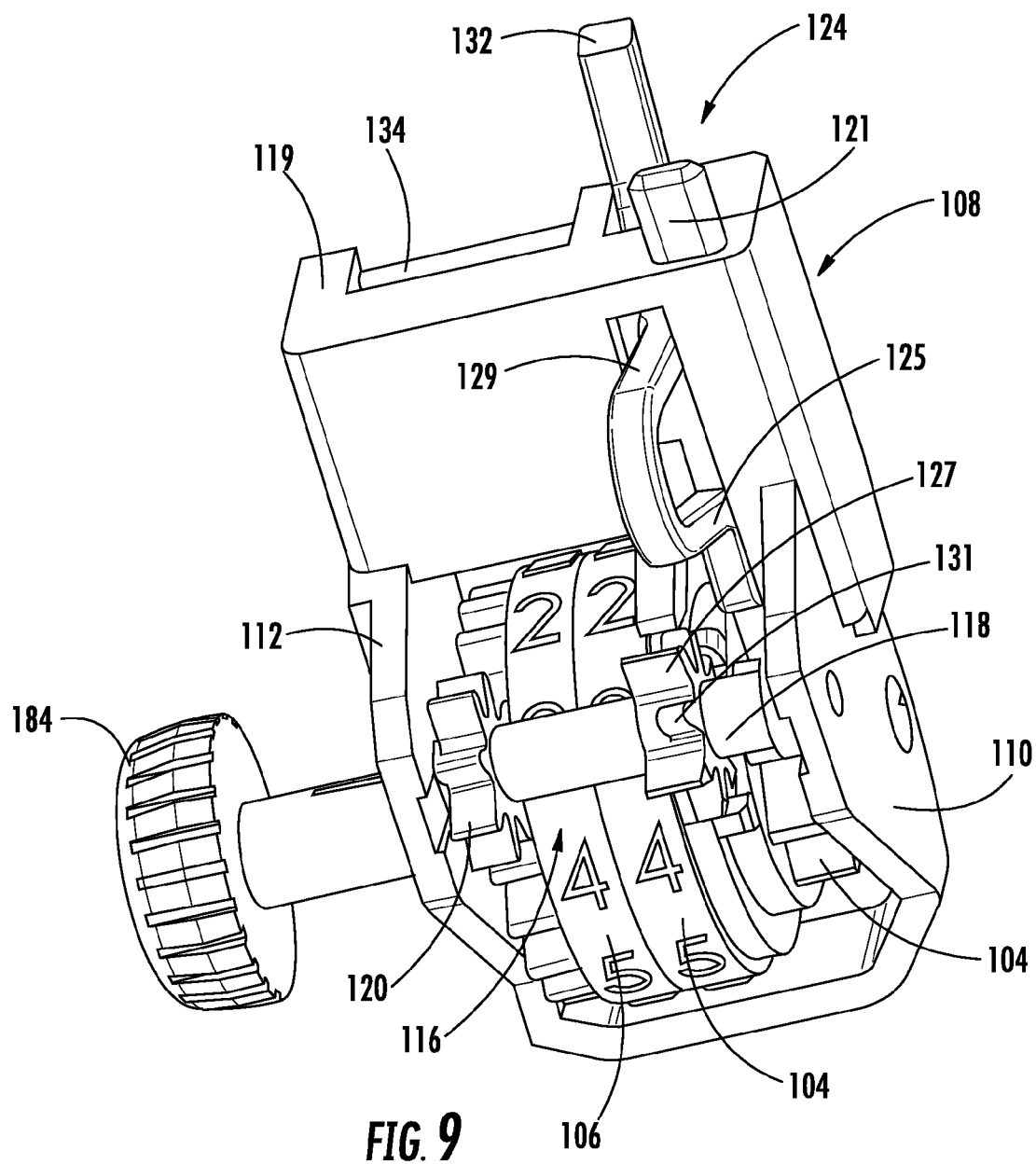
FIG. 9 is an isometric view from below of the event counter of FIG. 8.
Figure 10:
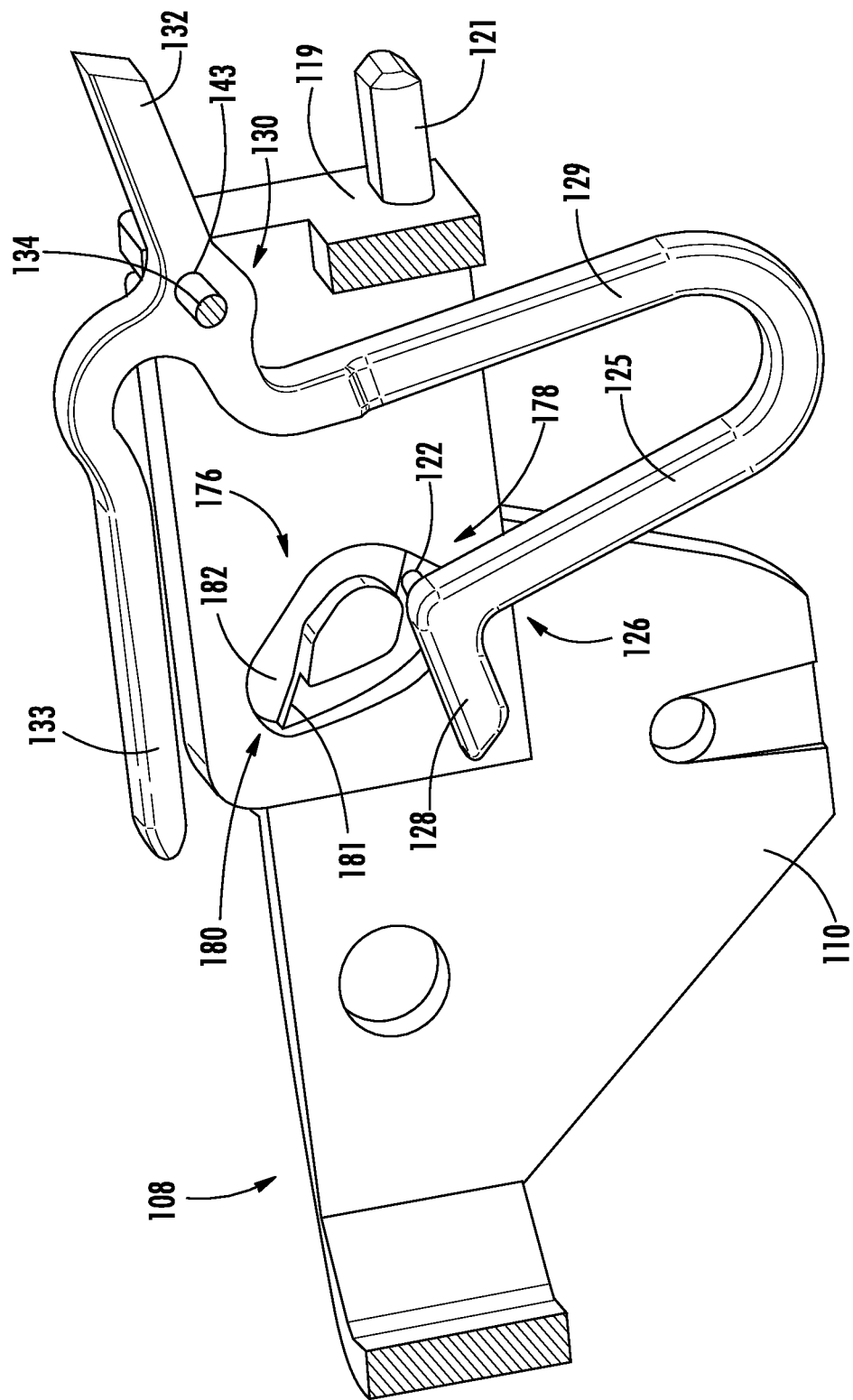
FIG. 10 is a section view of the event counter assembly of FIG. 8.
Figure 11:
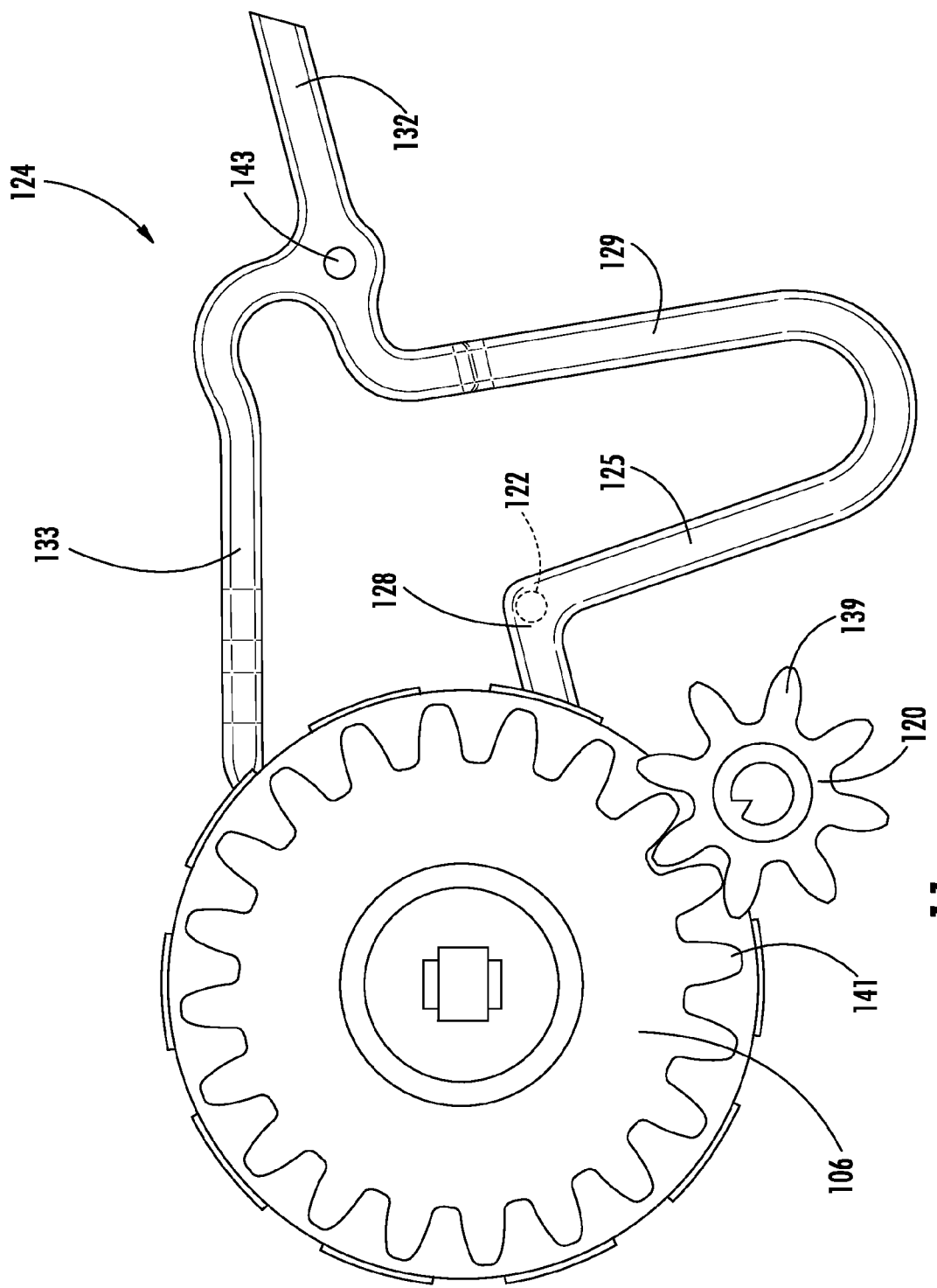
FIG. 11 is an elevation view of the second number wheel and advancement member.
Figure 12:
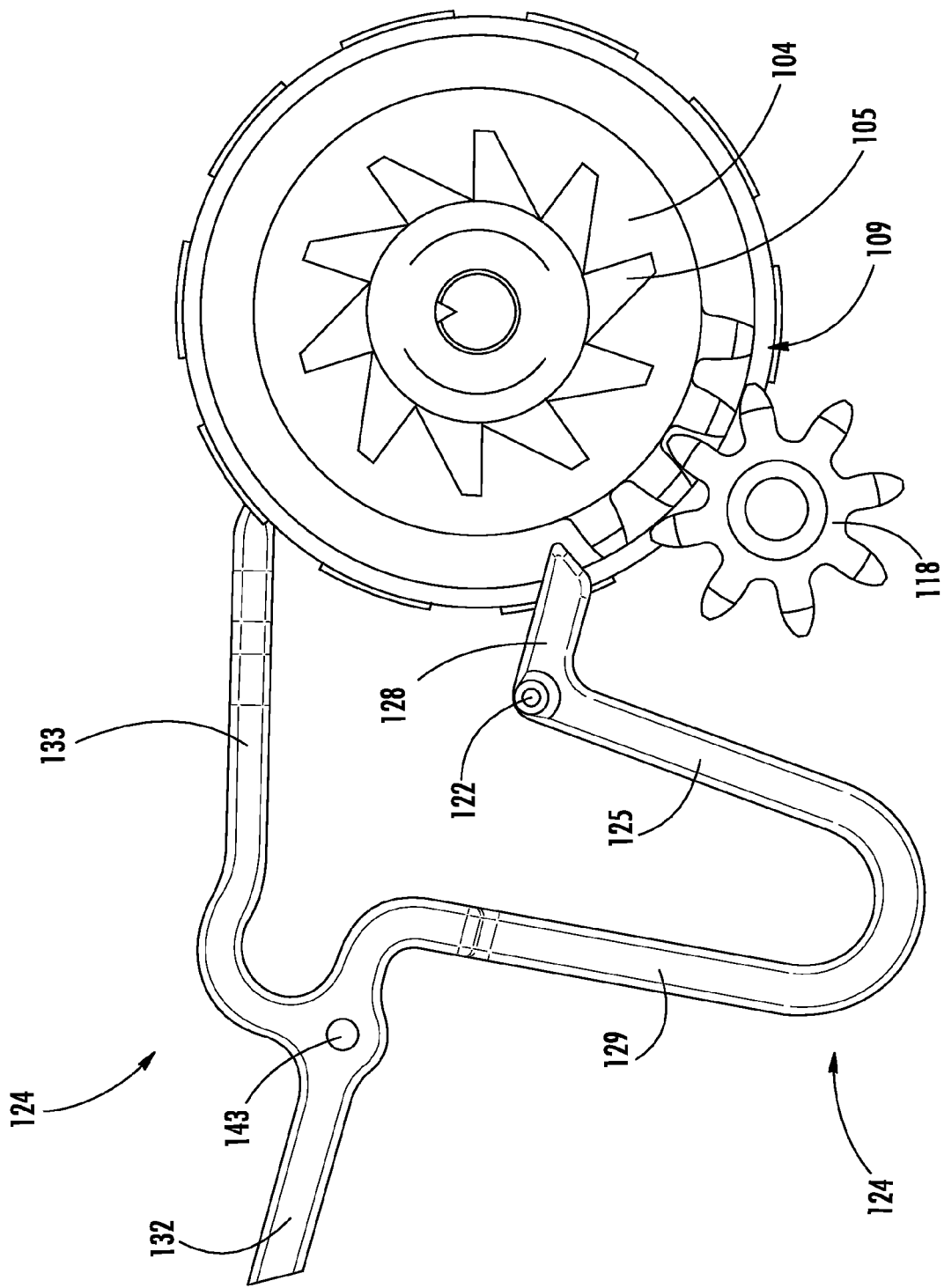
FIG. 12 is an elevation view of the first number wheel and advancement member.
Figure 13:
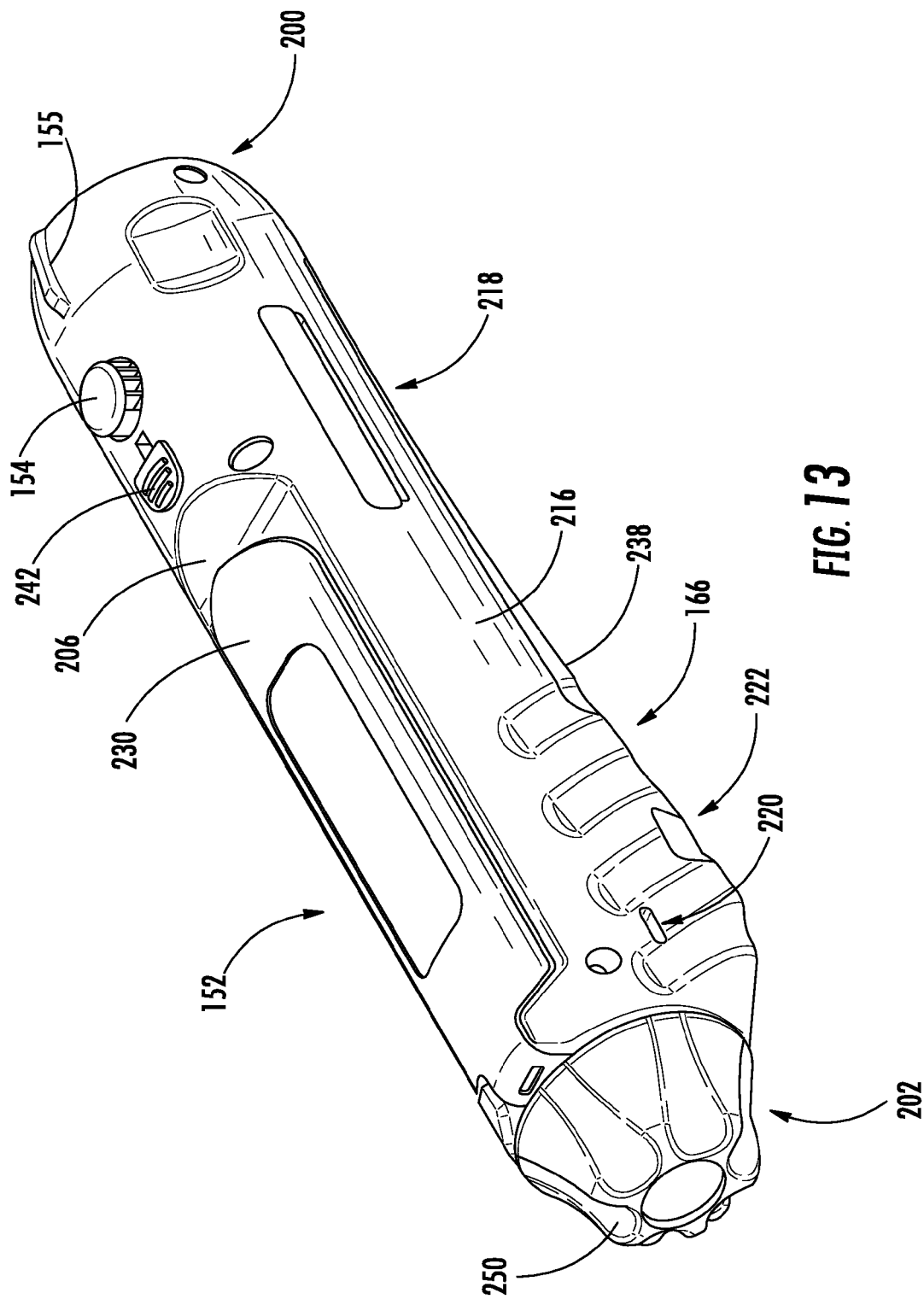
FIG. 13 is an isometric view from above of the rear of a biopsy needle actuator embodying aspects of the disclosed subject matter.
Figure 14:
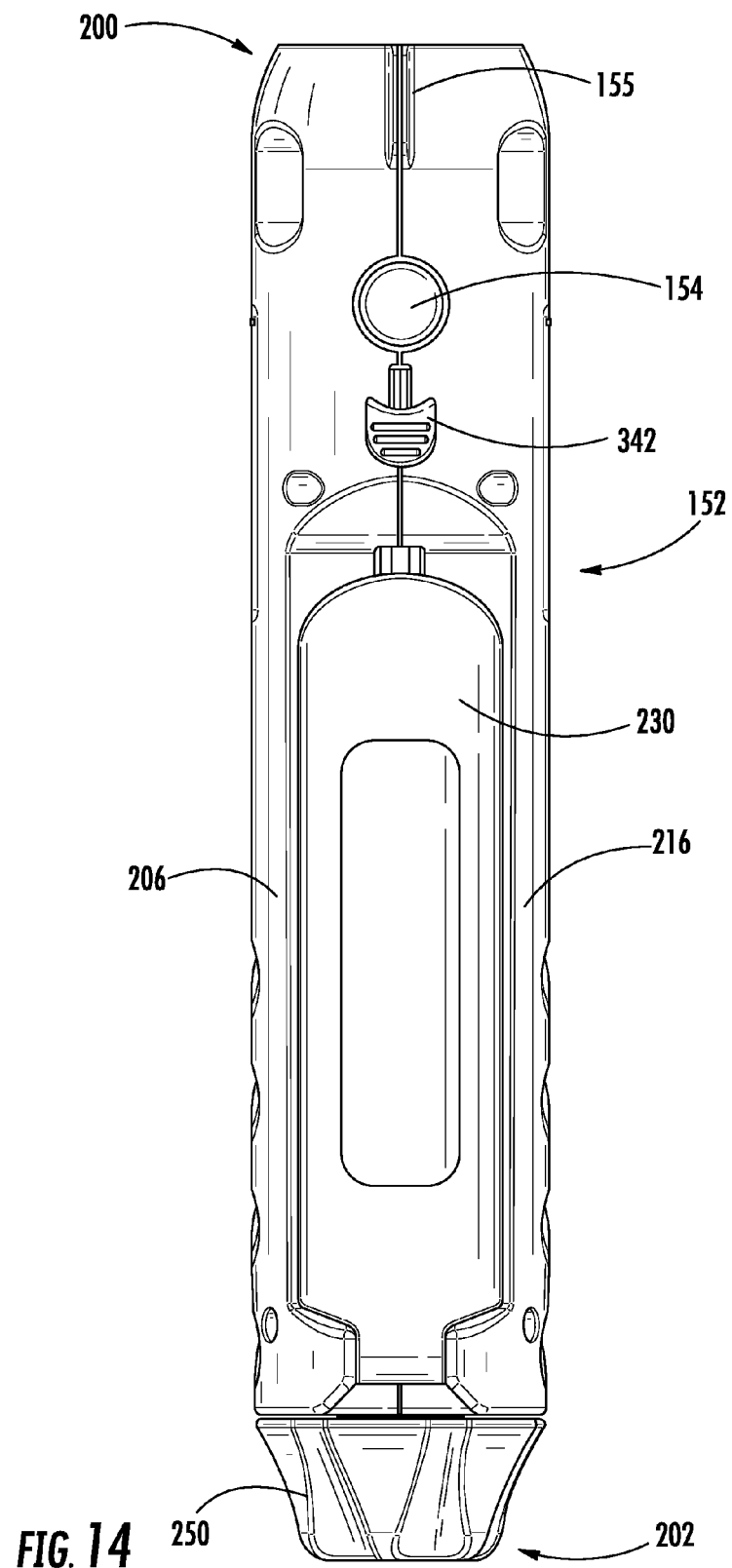
FIG. 14 is a top plan view of the actuator of FIG. 13.
Figure 15:
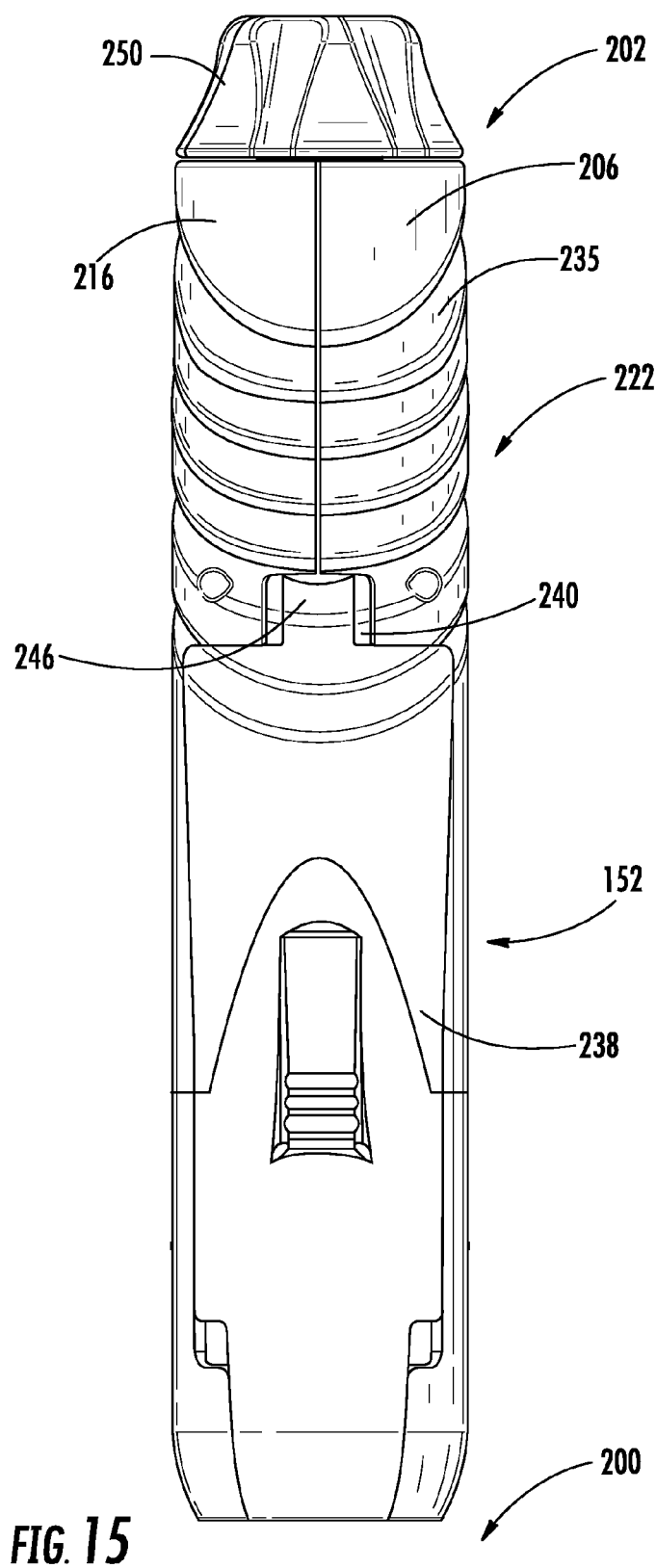
FIG. 15 is a bottom plan view of the actuator of FIG. 13.
Figure 16:
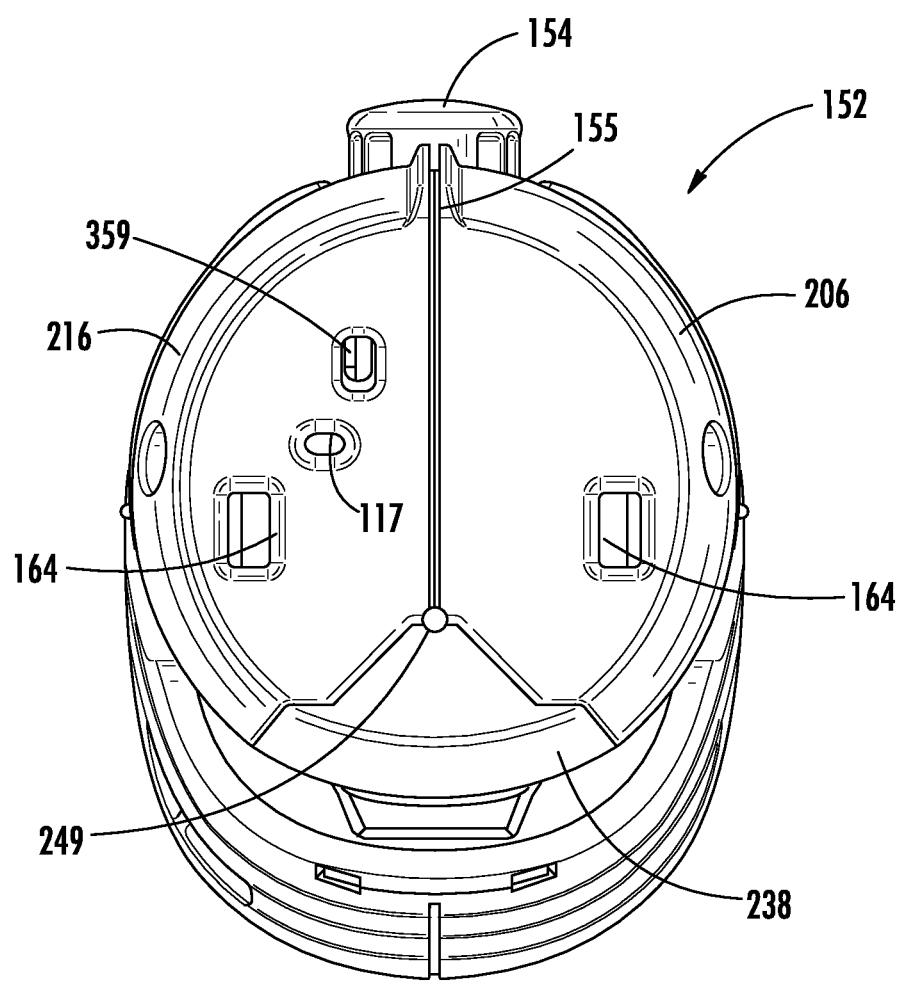
FIG. 16 is a front elevation view of the actuator of FIG. 13.
Figure 17:
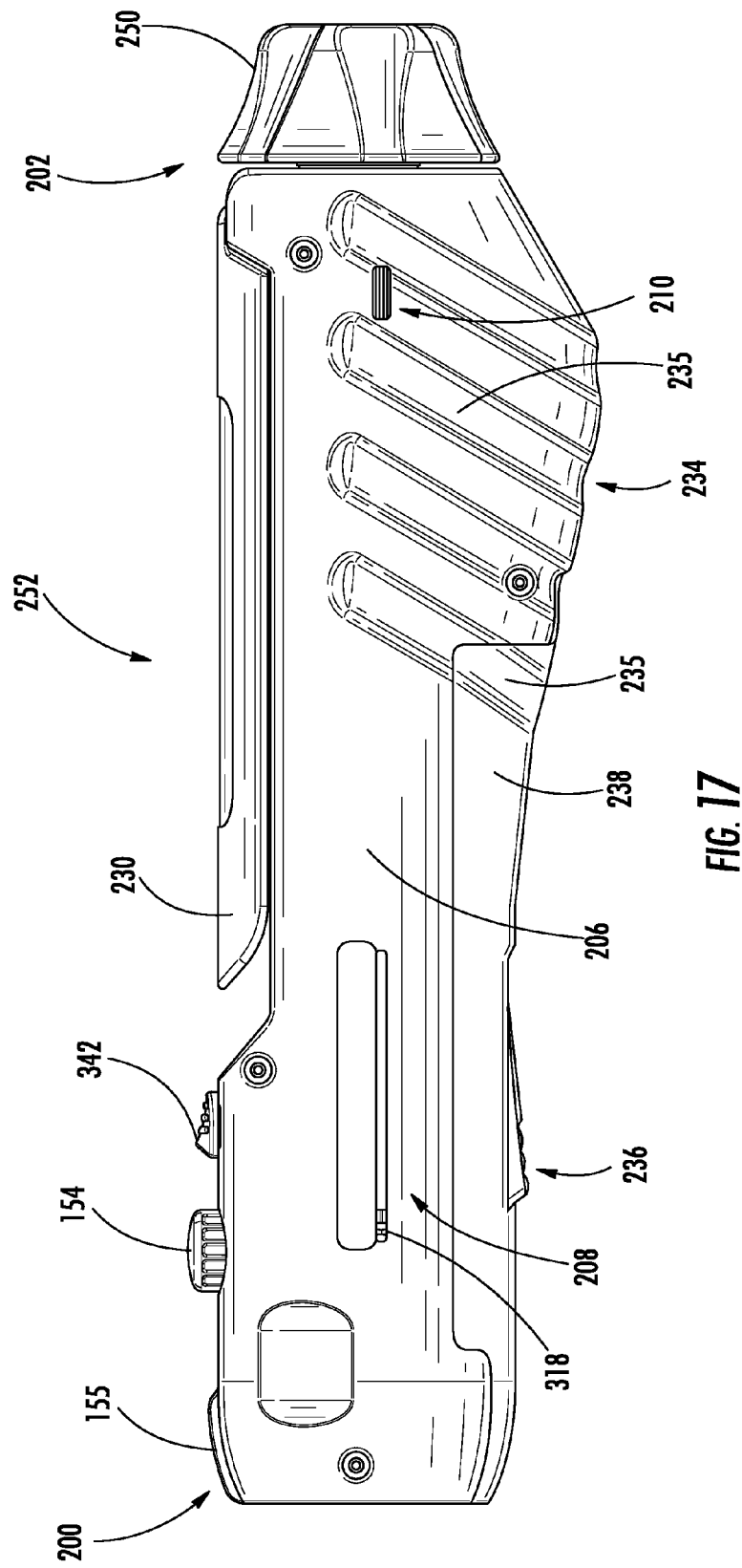
FIG. 17 is a left elevation view of the actuator of FIG. 13.

Referring to FIGS. 8-9, an indexing or counter gear assembly 116 adjacent the first and second number wheels 104, 106 moves the second number wheel 106. The indexing gear assembly 116 has a first index wheel 118 and a second index wheel 120 connected by a pivot pin 137. The pivot pin 137 extends between the first side 110 and second side 112, residing within an aperture in each side. The first index wheel 118 forms an alternating full-width tooth 127 and half-width tooth 131 at an outer edge, and a central opening with a key. Each half-width tooth is adjacent the first side 110 and engages an index gear set 109 formed by the first number wheel 104. The first index wheel 118 key engages a keyway in the shaft of the pivot pin 137, similar to the arrangement of keyway 123 in pin 135.

The second index wheel 120 forms teeth 139 at an outer edge, and a central opening with a key. The second index wheel 120 key engages the keyway in the shaft of the pivot pin 137 allowing the first and second index wheels 118, 120 to rotate together. The teeth 139 engage teeth 141 formed by the second index wheel 106. The first index wheel 118 rotates when it engages the teeth of an index gear set 109 in the first number wheel 104, rotating the second index wheel 120, and in turn the second number wheel 106, advancing the second number wheel 106 one digit.

When the actuator 152 is in use, the number wheels 104, 106 are rotated by movement of the advancement member 124 into engagement with teeth 105 on the first number wheel 104. The advancement member 124 is operably connected to the firing mechanism 156 of the actuator 152. In an embodiment, the advancement member 124 is generally U-shaped forming a first end 126 at the end of a first upright arm 125. The first end 126 forms a pawl member 128 that engages the teeth 105 of the first number wheel 104. Opposite the first upright arm 125 is a second upright arm 129. The second upright arm 129 forms a pivot 143 at a second end 130. An extension arm 132 and a spring arm 133 extend from the second end 130. When the counter assembly is joined with an actuator 152 the extension arm 132 extends into the body of the actuator 152 through an extension arm opening 359, and operably engages the firing mechanism of the actuator 152. The advancement member 124 rotates about a pivot pin 134 connected to the mount 108, whereby movement of the extension arm 132 from a first position to a second position moves the pawl 128 along a guide 176 and biases the spring arm 133 against the inside of the housing 101 creating a biasing force.

The guide 176 is formed by the first side 110 adjacent the advancement member 124. In an implementation the guide 176 is generally a tri-oval shaped channel forming a front portion connected to a rear portion forming an angular inner wall 182. The front portion begins at a first end 178 and ends at a second end 180. The advancement member 124 forms a pin 122 extending into and engaging the channel, with the pin 122 moving within the guide 176. The inner wall 182 of the front portion transitions from the first end 178 to the second end 180 extending laterally from the first end 178 terminating in a step 181. The inner wall 182 of the rear portion transitions from the second end 180 to the first end 178 extending laterally from the second end 180. As the extension arm 132 is moved from the first position to a second position, the pin 122 moves within the front portion from the first end 178 to the second end 180 urging the first end 126 laterally toward the second side 112, the pawl member 128 moves upward and forward toward the teeth 105 into engagement with a tooth 105, and the spring arm 133 biases against the housing 101 and the force of depressing the firing button 154. As the first end 126 moves away from the second end 130 the U-shaped advancement member 124 is put in tension. Engagement of the pawl 128 with the teeth 105 rotates the first number wheel 104 and the number wheel pivot pin 135 advancing the number displayed in the window 162 one digit. When the pin 122 reaches the second end 180 the pawl member 128 moves away from the teeth 105.

As the pin 122 passes through the second end 180 the pin 122 moves across the step 181 in the inner wall and laterally toward the first side 110, with the step preventing the pin 122 from moving within the front portion from the second end 180 to the first end 178. After passing the step 181 the tension formed within the U-shaped portion of the advancement member 124 disengages the pawl 128 from the teeth 105. Releasing pressure on the firing button 154 allows the extension arm 132 to move from the second position back to the first position, thereby moving the pin 122 within the rear portion of the guide 176 from the second end 180 to the first end 178 as the extension arm 132 moves from the second position, returning to the first position, whereby the firing button 154 is ready to be depressed again, and the pawl 128 is positioned to engage a tooth 105.

The housing 101 attaches to the front of a biopsy needle actuator 152 with locking tabs 103 that engage recesses 164 within the front of the actuator 152 housing 166. In an embodiment, the housing 101 is formed by the first end 200 of the actuator 152 thereby making the event counter 100 integral to the actuator 152. The housing 101 may be formed from plastic and extends from a front portion 107 to a rear portion 111. The rear portion 111 forms an opening allowing insertion of the counter assembly and the fitting of a rear cover 114. The edges of the rear cover 114 form tabs that engage notches on the housing 101 to retain the cover 114 within the rear portion 111. A passage 102 formed within the housing 101 allows room for the needle assembly 158 to exit the actuator 152. A frame opening 117 allows an alignment tab 121 extending from the rear portion 119 of the mount 108 and the extension arm 132 to engage openings in the front of the actuator 152 housing.

In an embodiment, a first fire lever 356 connected to the firing button 154 engages the advancement member 124, moving the fire lever 356 and moving the first number wheel 104 upon firing the biopsy needle 158. In an embodiment, the extension arm 132 extends from the event counter 100 housing 101 through a cover 114 into the housing 166 of the biopsy needle actuator 152, engaging the fire lever 160.

Figure 25:
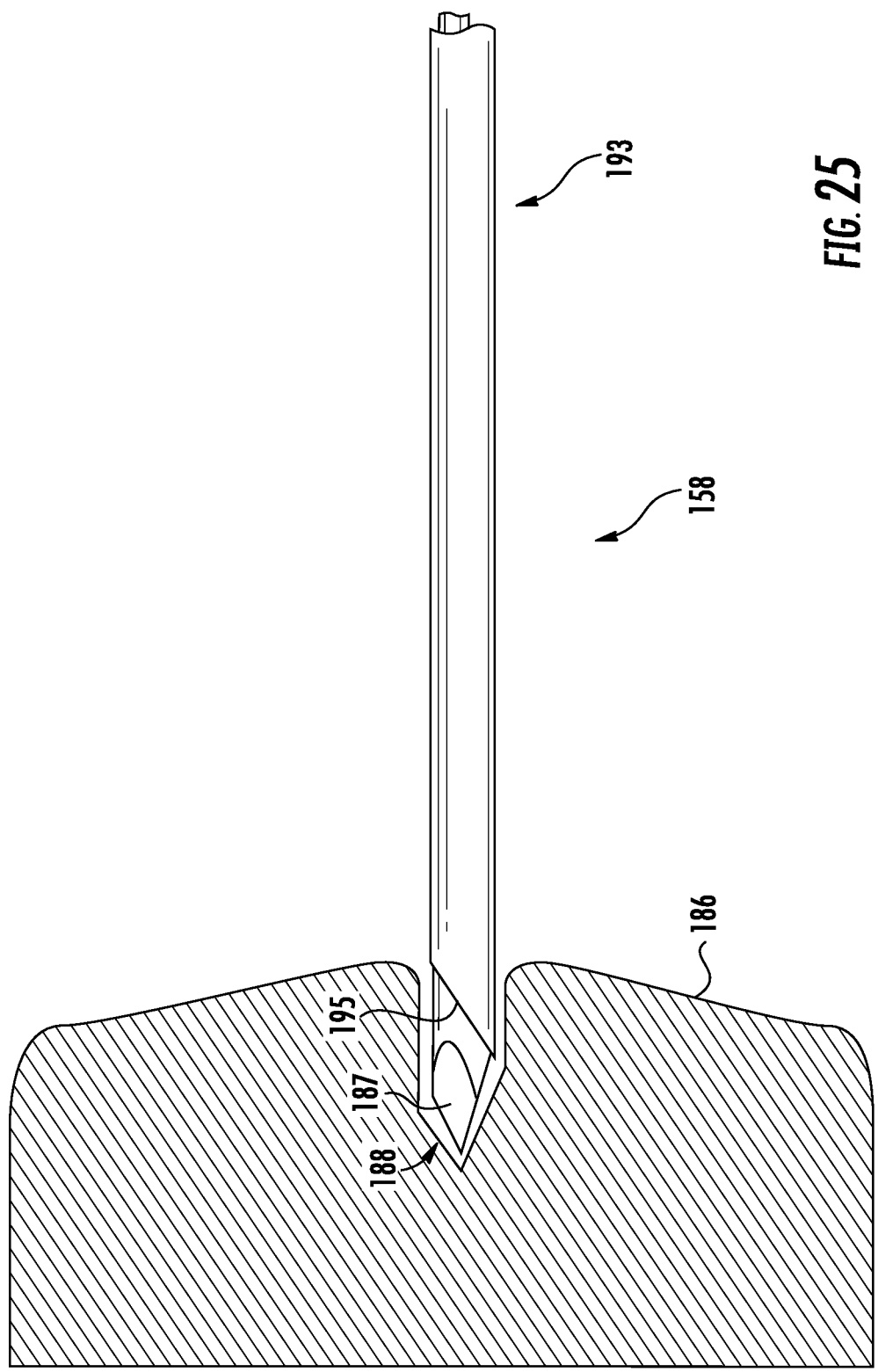
FIG. 25 is an elevation view showing a biopsy needle assembly in an armed condition with the tip in a target tissue.
Figure 26:
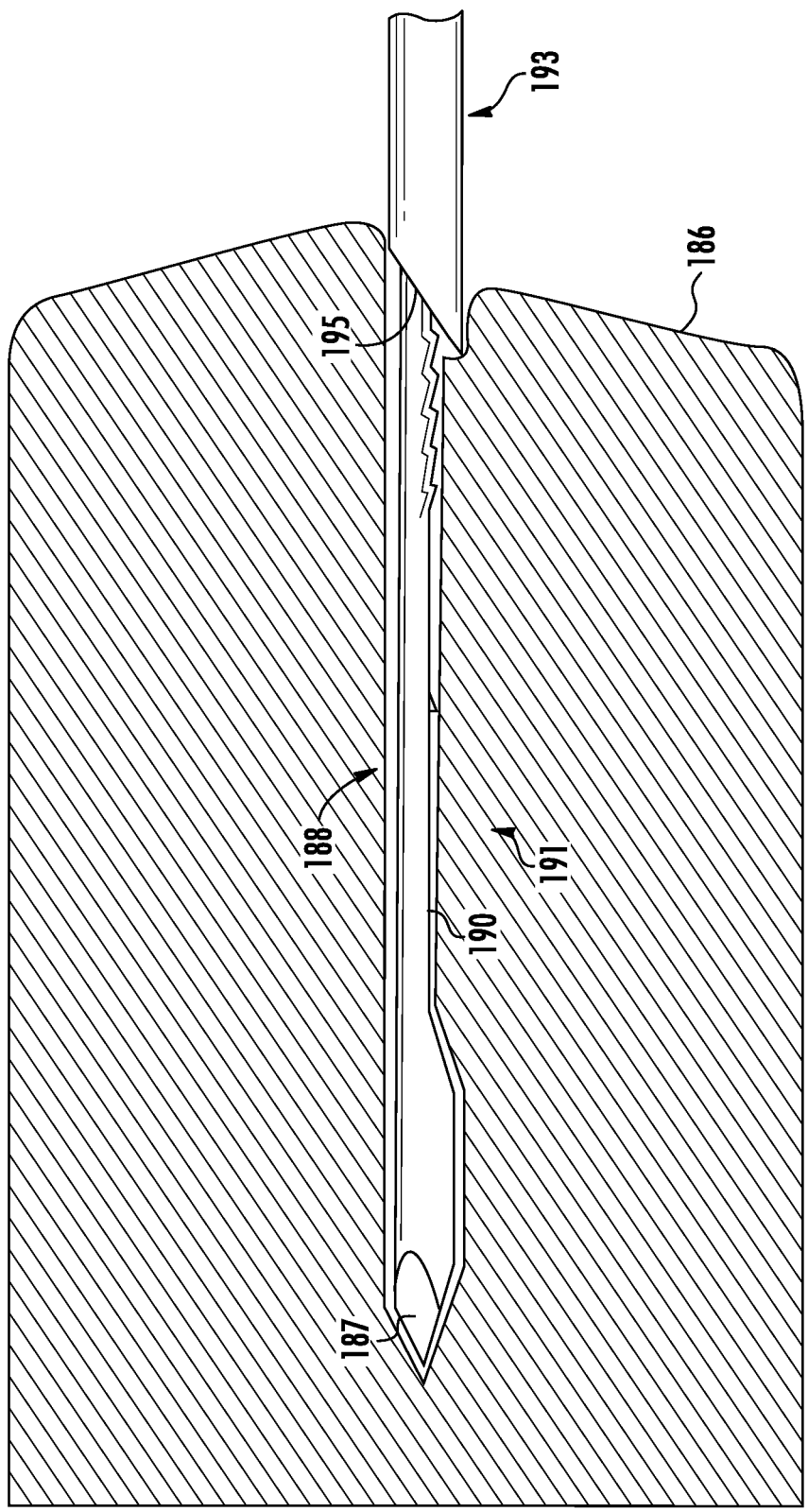
FIG. 26 is an elevation view showing a biopsy needle assembly where the needle carrier is in a fired condition.
Figure 27:
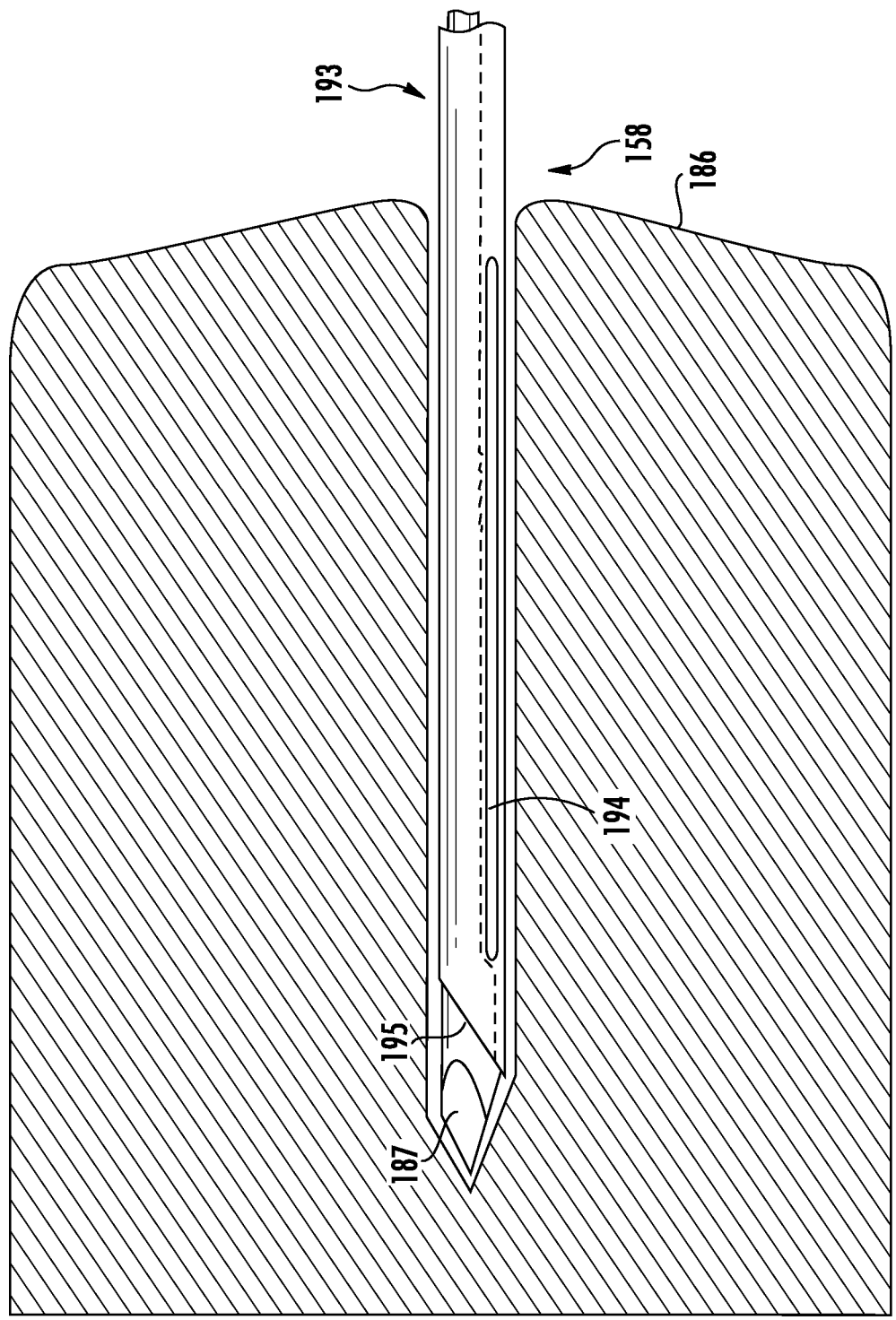
FIG. 27 is an elevation view showing a biopsy needle assembly with the needle carrier and the cannula carrier in a fired condition with a captured tissue specimen.

Referring to FIGS. 13-24, 29-31 and 33, a biopsy needle actuator 152 is shown and described. The actuator 152 controls use of the biopsy needle assembly 158 when excising a biopsy tissue specimen 194 from a target tissue 186 (FIGS. 25-27). The actuator 152 is capable of taking precise lengths of tissue samples using the biopsy needle assembly 158. The actuator 152 generally includes a needle firing safety assembly and a lifecycle indicator assembly 138.

Referring to FIGS. 13-17, the actuator 152 extends from a first or font end 200 to a second or rear end 202. The actuator 152 body or housing 166 is formed from a first or left body 206 joined to a second or right body 216, and a handle body door 238. The handle body door 238 movably joined to the left and right body 206, 216 at the bottom of the actuator 152 by a door hinge insert 240 allows a user access to the interior of the actuator 152 for inserting and removing a biopsy needle assembly 158. A loading lever 230 moveably jointed to the left and right body 206, 216 at the top rear end 202 of the actuator 152 rotates about a lever pivot pin 232 allowing a user to grasp the front end of the loading lever 230 and pull the lever 230 away from the housing 166 to move a cannula carrier 260 and needle carrier 278 from a first or fired position into a second charged or armed position ready for firing. A safety switch 342 and a fire button 154 are accessible at the top of the actuator 154.

The left body 206 includes a throw length gauge 208 near the front end 200 displaying the throw length or distance the needle carrier 278 and cannula carrier 260 will travel with the needle assembly 158 between an armed position and a fired position. The throw length is adjusted by a user using a biopsy needle depth control member or knob 250 at the rear end 202 of the actuator 152. Rotating the depth control knob 250 positions a stop plate 316 within the actuator 152 between a distance of about 20 mm to about 60 mm from the end of the needle and cannula carriers 278, 260 when the carriers are in an armed position. The length of the throw length can be adjusted by the user to take specific length of biopsy specimen depending upon the shape of the target tissue being sampled, thereby avoiding taking a biopsy specimen that is longer than desired or shorter than desired. A tab 318 formed by the stop plate 316 extends toward the left body 206 is visible within a window framed by markings on the left body 206 indicating the distance of about 20 mm to about 60 mm in one millimeter increments. The left body 206 includes an armed indicator 210 near the rear end 202. A fin 266 at the rear of the cannula carrier 260 appears within an aperture framed by the armed indicator 210 showing that the cannula carrier 260 is in the armed position.

The right body 216 includes a throw length gauge 218 near the front end 200 displaying the throw length of the needle carrier 278 and cannula carrier 260 in the same manner as accomplished at the left body 206. A tab 320 formed by the stop plate 316 extends toward the right body 216 is visible within a window framed by markings on the right body 216 indicating the distance of about 20 mm to about 60 mm in one millimeter increments. The right body 216 includes an armed indicator 220 near the rear end 202. A fin 284 at the rear of the needle carrier 278 appears within an aperture framed by the armed indicator 220 showing that the needle carrier 278 is in the armed position. The right body 216 further includes a lifecycle indicator window 222 showing the status of the life cycle indicator 142.

The actuator 152 is designed to fit comfortably in the hand of the user. The rear of the left body 206, handle body door 238, and right body 216 form a grip 234 with grooves 235 that partially circumscribe the housing 166. Each groove 235 extends from the midline of the left body 206 downward and forward to the underside of the actuator 152 continuing upward and rearward to the midline of the right body 216. The grooves 235 allow placement of one or more of the index finger, middle finger, ring finger, and baby finger of a user to aid in holding and orientating actuator 152 during use. The midsection of the handle body door 238 forms a forward and downward projecting protrusion finger rest 236 allowing a user to extend and rest their index finger providing additional grip and control of the actuator 152 when in use, and a surface to push on to disengage the handle body door 238 to access the interior of the housing 166 for inserting and removing needle assemblies 158.

Figure 18:
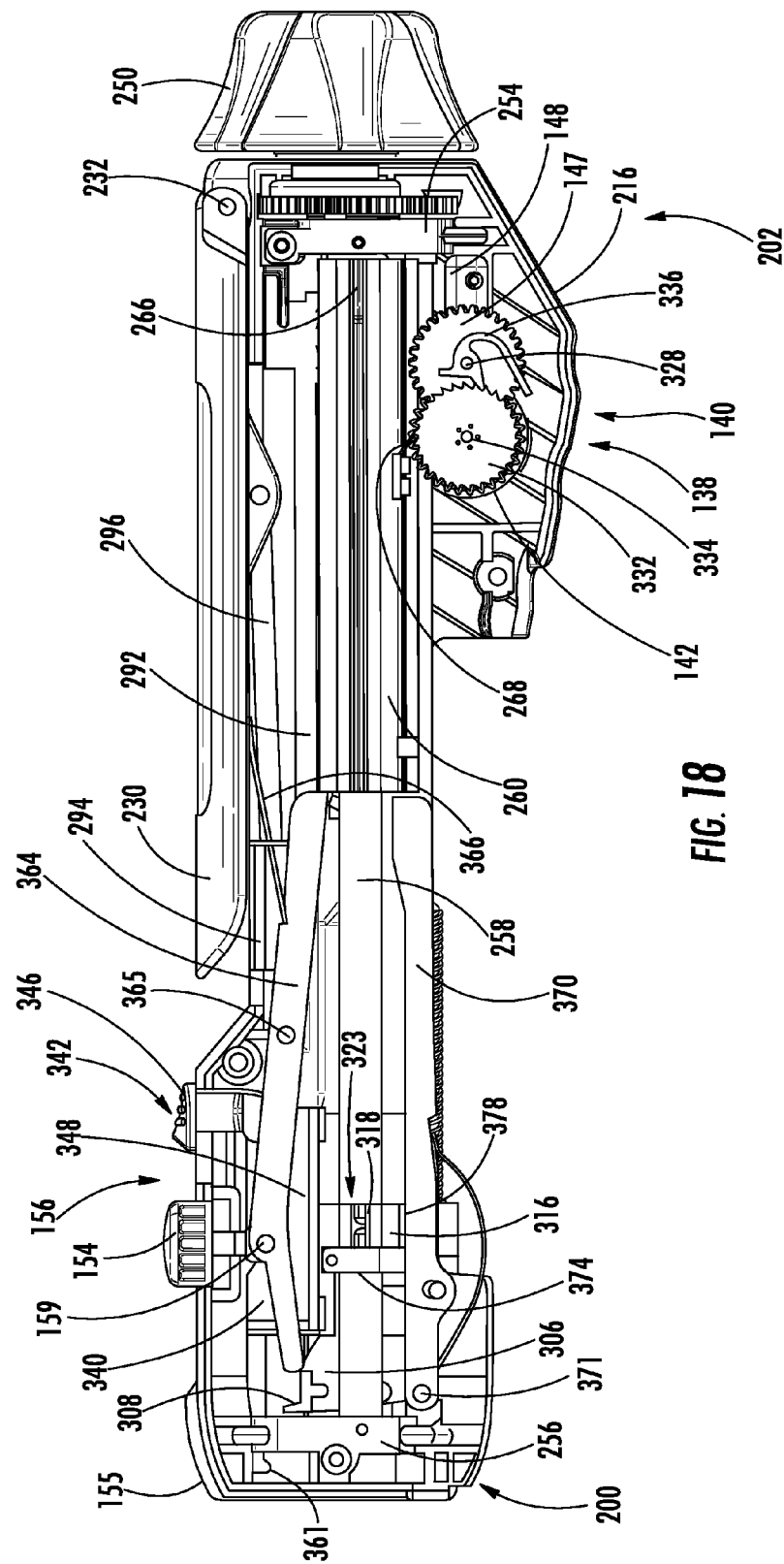
FIG. 18 shows the first body and handle body door removed from the actuator shown in FIG. 17.
Figure 19:
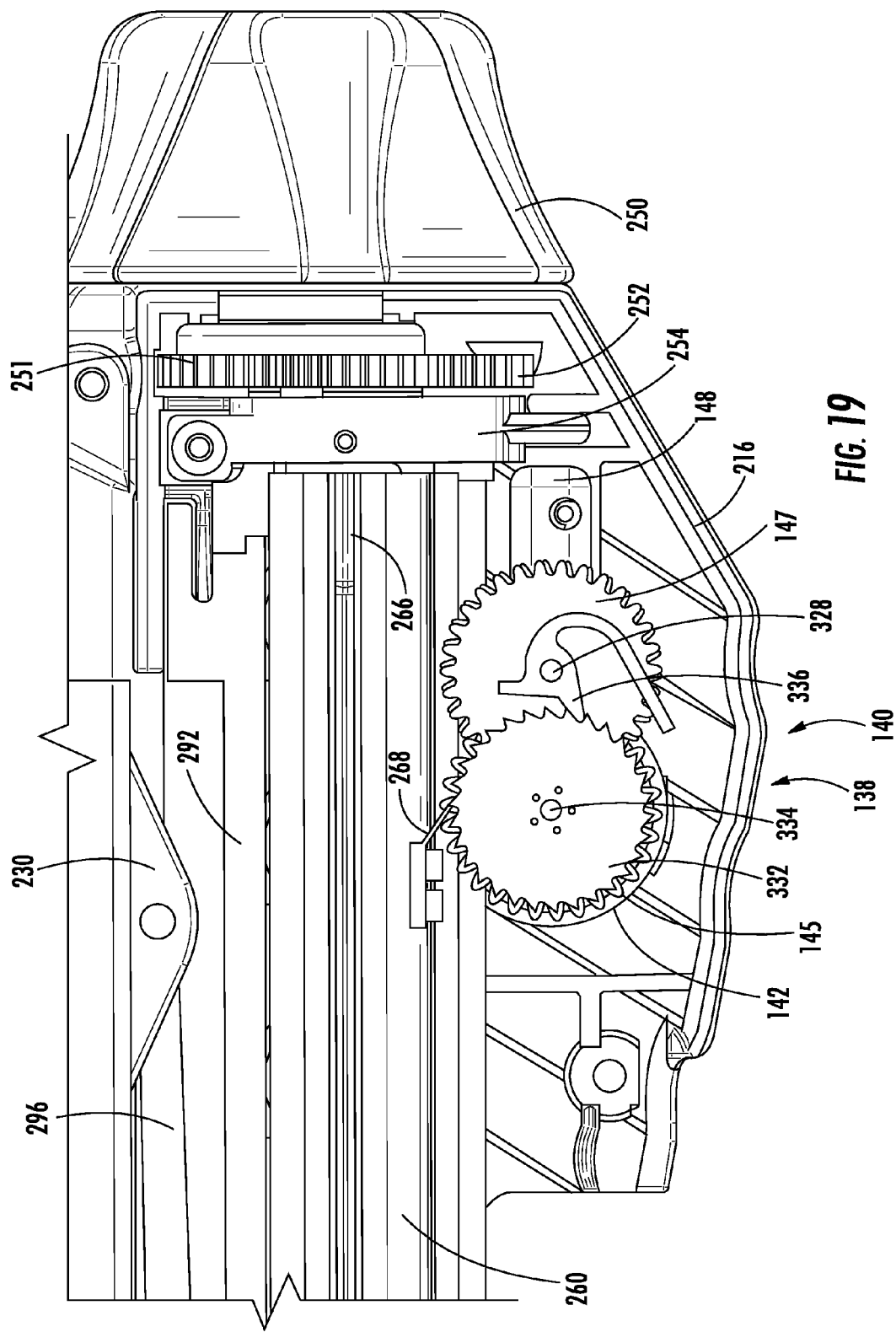
FIG. 19 is an enlarged view of the lifecycle indicator assembly of the actuator shown in FIG. 18.
Figure 20:
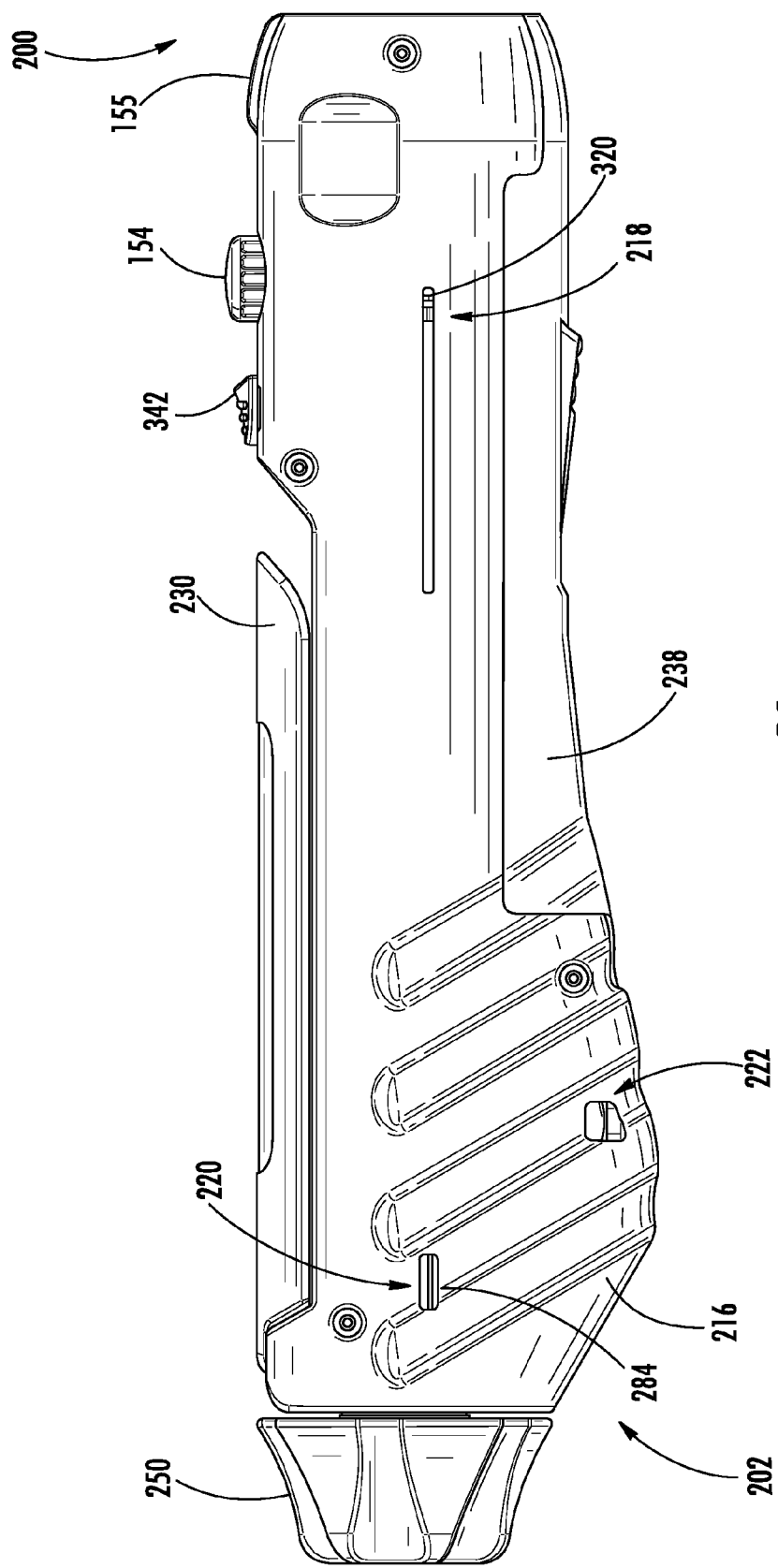
FIG. 20 is right elevation view of the actuator of FIG. 13.

FIG. 18 is a left elevation view of the actuator 152 with the left body 206 and handle body door 238 removed showing the mechanical components at the left side of the actuator 152 within the housing 166, with the cannula carrier 260 in the armed position. The cannula carrier 260 has an elongated body forming a tubular passage 262 extending from a front end to a rear end, a puller catch contact 264 at the rear end, and the fin 266 extending from the side of the body at the rear end. An insert 270 within the passage 262 at the front end of the cannula carrier 260 retains a helical spring 272 within the passage 262. The cannula carrier 260 travels along a guide shaft 258 extending between a front plate 256 and a back plate 254. The guide shaft 258 may be formed from a self-lubricating or low friction material hard anodized aluminum, or TEFLON® impregnated material. The cannula carrier 260 travels along the guide shaft 258 between the stop plate 316 and the back plate 254. Upon arming the actuator 152, the spring 272 compresses between the insert 270 and back plate 254 providing a force for advancing the cannula carrier 260 and cannula 193 connected thereto between the armed position and the fired position. A projection forming a life cycle ratchet pusher 268 extends from the cannula carrier 260 for advancing a life cycle indicator assembly 138.

The life cycle indicator assembly 138 registers arming of the cannula carrier 260 to show the cumulative use of the actuator 152, and alerting the user to replace or service the indicator before function is impaired. The indicator assembly 138 includes a lifecycle indicator 142 operably connected to a ratchet gear assembly 332 and idler gear assembly 140. Mechanical biopsy needle actuators 152 have moveable parts that can wear out affecting the operation and accuracy of the device. The lifecycle indicator 142 provides visual information to a user indicating when the actuator 152 is at or nearing the end of its recommended useful life. In an embodiment, the lifecycle indicator 142 changes from a first field 198, or the color green to a second field 199, or the color red to indicate the actuator 152 has reached the end of its useful life. The colors may be formed from anodized aluminum. The lifecycle indicator assembly 138 registers a change upon the occurrence of an event involving the actuator 152. In an embodiment, the lifecycle indicator 142 registers a change including when the biopsy needle assembly 158 is charged or fired, such as when the needle 188 is charged, when the needle 188 is fired, when the cannula 193 is charged, or when the cannula 193 is fired.

The idler gear assembly 140 includes a first idler gear assembly 145 that engages a second idler gear assembly 147. The rate of change of the lifecycle indicator 142 can accommodate any number of events involving the instrument. In an embodiment, a gear assembly 140 including a series of large and small gears are used, employing gears of different ratios of teeth, in different combinations, to achieve a given lifecycle result. For example, if the actuator 152 is rated for 15,000 events denoting 15,000 movements of a mechanical component of the instrument, gears with a particular number of teeth can be used to rotate a lifecycle indicator 142 to represent a given lifecycle result.

The indicator wheel 144, on the right side of the actuator 152 body, is operably connected to the first idler assembly 145 and the ratchet gear assembly 332 by a shaft 334. The shaft 334 extends from a first to a second end, passing through a support 148 connected to the left body 206. The support is positioned between the indicator 144 and first idler assembly 145. The first idler assembly 145 is between the support 148 and the ratchet gear assembly 332. The ratchet gear assembly 332 is at the first end of the shaft 334 and includes teeth at its peripheral edge. The first idler assembly 145 includes large gears that engage small gears on the second idler assembly 147, and small gears that engage large gears on the second idler assembly 147. An idler gear shaft 328 extends from a first end to a second end connecting the second idler assembly 147 to the support 148. The ratchet pusher 268 engages the teeth at the top of the ratchet gear assembly 332 each time the cannula carrier 260 is moved from the fired position to the armed position, rotating the indicator 144. A pawl member 336, mounted to the idler gear shaft 328, and biased against the interior left body 206, engages the teeth of the ratchet gear assembly 332 allowing the ratchet gear assembly 332 to rotate in a first direction when cannula carrier 260 is moved from the fired position to the armed position, but inhibits rotation of the ratchet gear assembly 332 in a second or opposite direction when the cannula carrier 260 moves in the opposite direction from the armed position to the fired position. As the actuator 152 is charged or armed during procedures, the indicator wheel 144 rotates. The indicator wheel presents a first field 198 and a second field 199. In an embodiment, the first field 198 is a first color, and the second field 199 is a second color. Repeatedly arming the actuator 152 rotates the wheel 144 gradually transitioning the wheel 144 at a reference point from the first field 198 to the second field 199. In an embodiment, upon each charge of the actuator 152, gradually transitioning the visible color of the indicator wheel 144 framed by, and visible through, the lifecycle indicator window 222 transitions from the first field 198, or the color green to a partial green, and ultimately to the second field 199, or the color red. When the actuator 152 has reached the end of its useful life, the color of the indicator wheel 144 visible through the window 222 of the housing 166 will be entirely the second field 199, or the color red.

Figure 21:
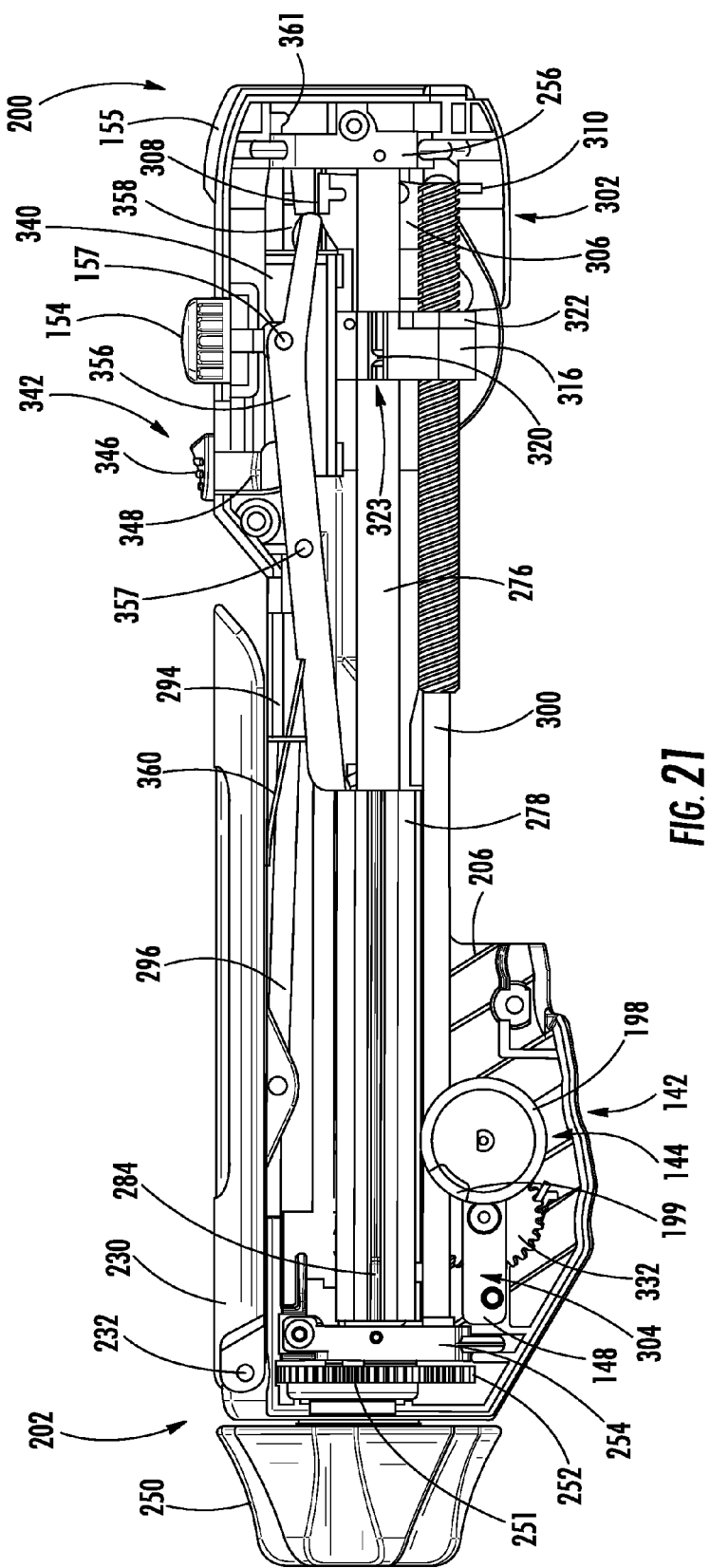
FIG. 21 shows the second body and handle body door removed from the actuator shown in FIG. 20.
Figure 22:
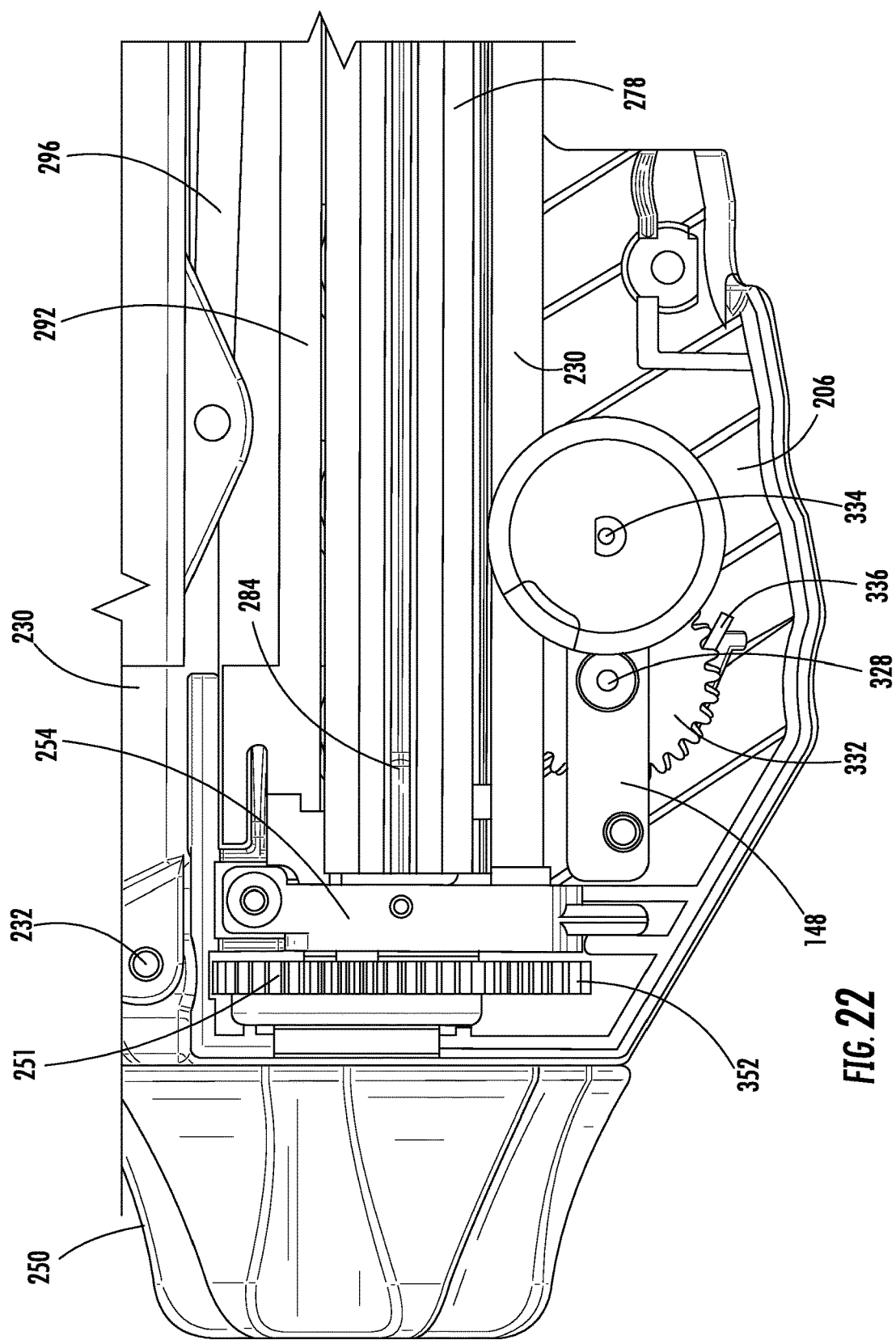
FIG. 22 is an enlarged view of the lifecycle indicator assembly of the actuator shown in FIG. 22.

FIG. 21 is a right elevation view of the actuator 152 with the right body 216 and handle body door 238 removed showing the mechanical components at the right side of the actuator 152 within the body, with the needle carrier 278 in the armed position. The needle carrier 278 has an elongated body forming a tubular passage 280 extending from a front end to a rear end, a puller catch contact 282 at a rear end, and the fin 284 extending from the side of the body at the rear end. An insert 286 within the passage 280 at the front end of the needle carrier 278 retains a helical spring 288 within the passage 280. The needle carrier 278 travels along a guide shaft 276 extending between the front plate 256 and the back plate 254. The guide shaft 276 is adjacent guide shaft 258, and may be formed having the same properties as shaft 258. The needle carrier travels along the guide shaft 276 between the stop plate 316 and the back plate 254. Upon arming the actuator 152, the spring 288 compresses between the insert 286 and back plate 254 providing a force for advancing the needle carrier 278 and needle 188 between the armed position and the fired position.

Below the guide shaft 276 is a stop lead screw 300. The lead screw extends from a first end 302 rotatably mounted to the front plate 256, and a second end 304, rotatably mounted to the back plate 254. The first end 302 is threadably received by a lead screw nut 322 connected to the stop plate 316. Rotation of the lead screw 300 moves the stop plate 316 along guide shafts 258, 276 between the front plate 256 and the back plate 254. The distance in centimeters from the rear of the stop plate 316 and the front of the cannula carrier 260 and needle carrier 278 is shown to the user by reference to the throw length gauges 208, 218. The second end 304 connects to a stop lead screw gear 252 at the rear of the back plate 256. The stop lead screw gear 252 engages a depth control nob gear 251 rotatably mounted to the rear of the back plate 256. The depth control knob 250 is operably connected to the depth control nob gear 251. Rotation of the depth control knob 250 rotates the stop lead screw 300 adjusting the distance between the rear of the stop plate 316 and the front end of the carriers 260, 278 when the carriers are in the armed position, thereby determining the distance the cannula 193 and needle 188 will travel when the gun 152 is fired.

The cannula carrier 260 and needle carrier 278 are moved from the fired position to an armed position using the loading lever 230. Positioning the cannula carrier 260 in an armed position positions an attached cannula 193 in an armed position, and positioning the needle carrier 278 in an armed position positions an attached needle 188 in an armed position. The loading lever, 230 moveably jointed to the left and right body 206, 216 at the top rear end 202 of the actuator 152, rotates about the lever pivot pin 232 allowing a user to grasp the front end of the loading lever 230 to move the cannula carrier 260 and needle carrier 278 into a charged or armed position ready for firing. When the actuator 152 is in use, the loading lever 230 is in a first position flush with the actuator 152 body. At the fired or rest position the front surface of the carriers 260, 278 are in contact with the rear surface 323 of the stop plate 316. When the carriers 260, 278 are in a fired position, a needle assembly 158 can be inserted or removed from the actuator 152. Moving the loading lever 230 from a first position, to a second position where the lever 230 is extending from the body, moves the carriers 260, 278 from the fired position to the armed position.

A lever link 296 connects the loading lever 230 to a lever carrier 294 within the body. The lever carrier 294 moves along a lever carrier shaft 292, the lever carrier shaft 292 extends between the front plate 256 and the back plate 254 generally between the cannula carrier 260 and needle carrier 278. The lever carrier 294 moves between a lever safety 340 adjacent the front plate 256, and the back plate 254.

Figure 23:
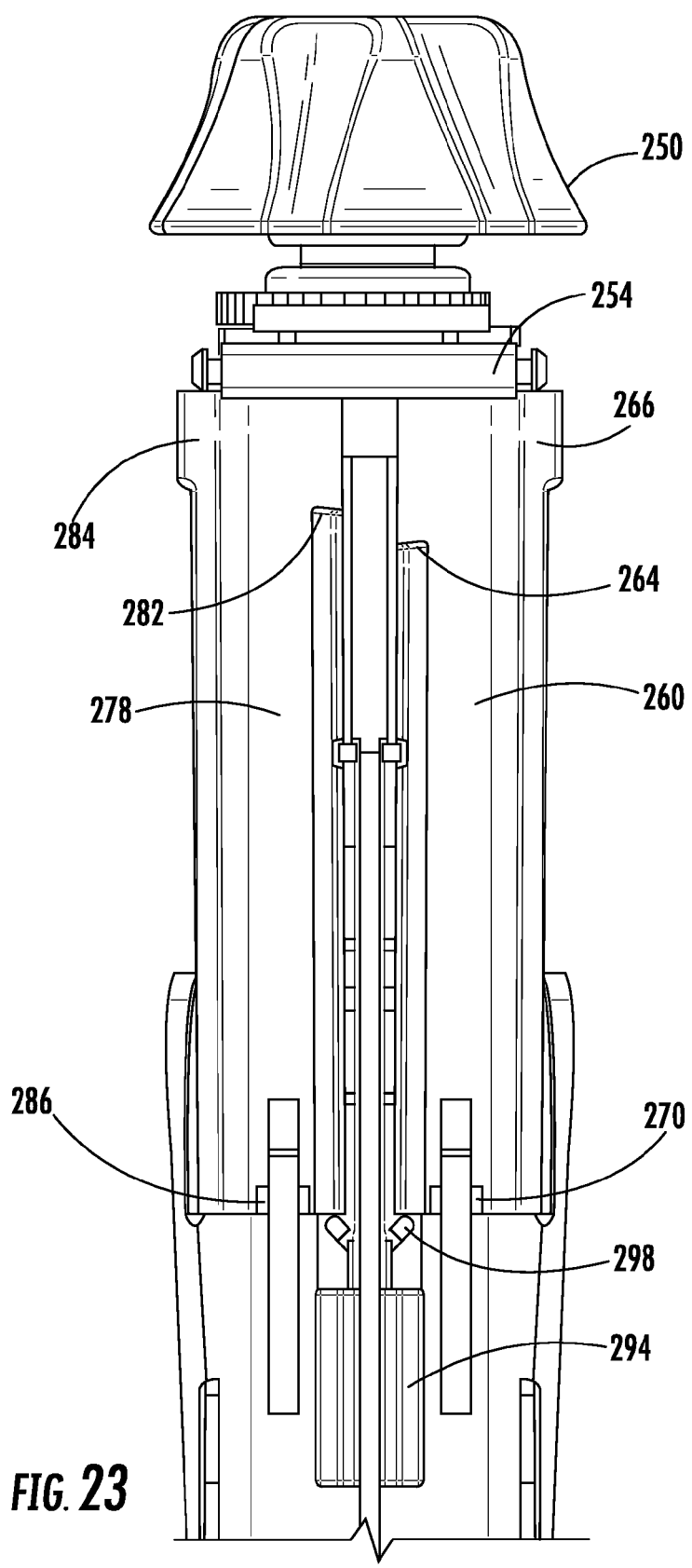
FIG. 23 shows the first and second body, and loading lever removed from the actuator shown in FIG. 14.
Figure 24:
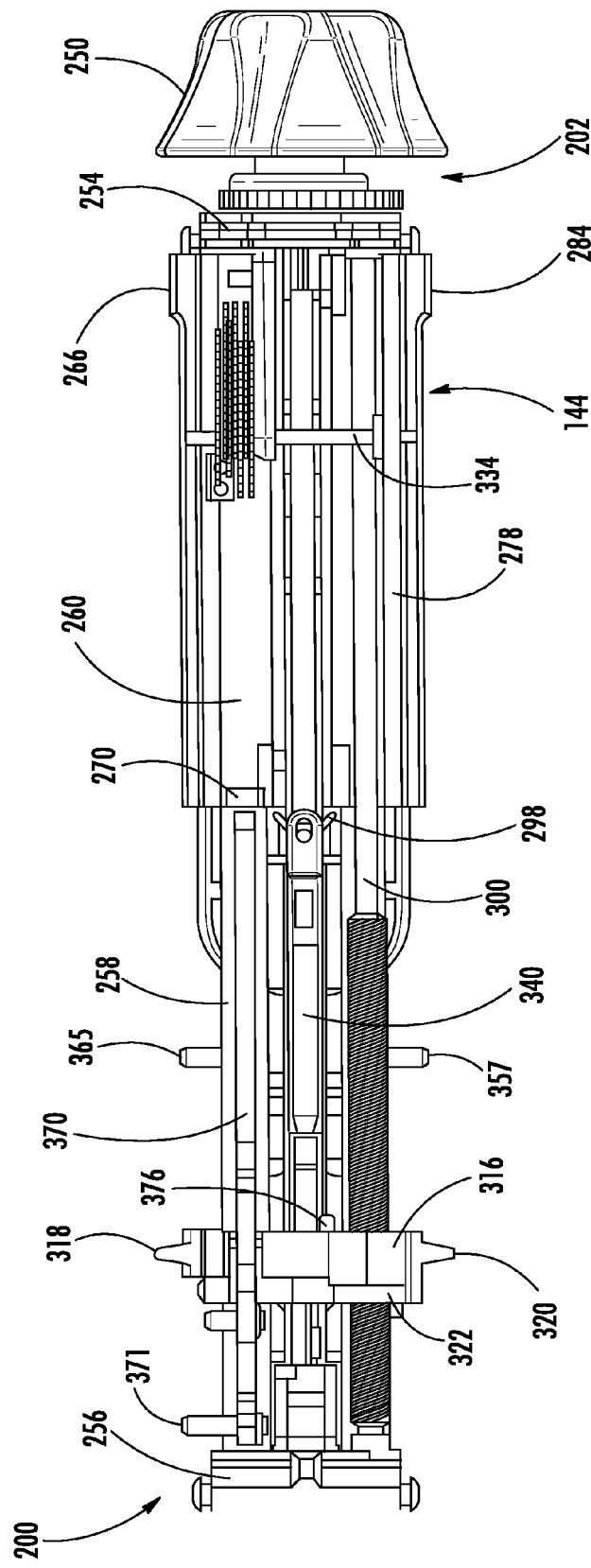
FIG. 24 shows the first and second body, and the handle body door removed from the actuator shown in FIG. 15.

Referring to FIGS. 23-24, the rear of the lever carrier 294 includes a puller catch 298 with a cannula carrier lobe and a needle carrier lobe that engage puller catch contact 264 and puller catch contact 282, respectively. The cannula carrier lobe extends at a right angle from the needle carrier lobe, and a catch spring biases the puller catch 298 forward into the rear of the lever carrier 294 whereby the puller catch 298 forms a V-shape at the rear of the lever carrier 294 when the puller catch 298 is at the rest position. The puller catch 298 rotates about a shaft. The puller catch contact 264 on the cannula carrier 260 is closer to the front of the cannula carrier 260 than the puller catch contact 282 of the needle carrier 278 is to the front of the needle carrier 278. When arming the actuator 152, a first pull of the loading lever 230 moves the lever carrier 294 rearward where the cannula carrier lobe of the puller catch 298 first engages the puller catch contact 264 causing the puller catch 298 to bias against the sidewall of the lever carrier 294 and rotate about the shaft and moving the needle carrier lobe toward the cannula carrier 260 and out of line with the puller catch contact 282. With the puller catch 298 in engagement with puller catch contact 264, moving the loading lever 230 to the second position moves the cannula carrier 260 and an attached cannula 193 rearward, compressing the spring 272, and arming the cannula carrier 260 for firing. After arming the cannula carrier 260, the cannula carrier 260 is held in the armed position by a second fire lever 364. Arming the cannula carrier 260 moves the cannula 193 rearward, exposing the core bed 190 of the needle 188. Upon arming of the cannula carrier 260, the fin 266 is visible in the armed indicator 210 showing the user that the cannula 193 is armed for firing. The loading lever 230 is then moved back to the first position, and the catch spring moves the puller catch 298 forward, returning the puller catch 298 to the rest position.

A second pull of the loading lever 230 engages the needle carrier lobe of the puller catch 298 with the puller catch contact 282 causing the puller catch 298 to bias against the sidewall of the lever carrier 294 and rotate about the shaft and moving the cannula carrier lobe toward the needle carrier 278 and out of line with the puller catch contact 264. With the puller catch 298 in engagement with the puller catch contact 282, moving the loading lever 230 to the second position moves the needle carrier 278 and the attached needle 188 rearward, compressing the spring 288, and arming the needle carrier 278 for firing. After arming the needle carrier 278, the needle carrier 278 is held in the armed position by a first fire lever 356. Arming the needle carrier 278 moves the needle 188 rearward within the cannula 193, covering the core bed 190 of the needle 188 with the shaft of the cannula 193. Upon arming of the needle carrier 278, the fin 284 is visible in the armed indicator 220, showing the user that the needle carrier 278 is armed for firing. The loading lever 230 is then moved back to the first position flush with the body 166, and the actuator 152 is ready for use excising a biopsy tissue specimen 194 from a target tissue 186. The actuator 152 is fired by actuating a firing mechanism 156 when the cannula carrier 260 and needle carrier 278 are in their armed positions.

The firing mechanism 156 includes, in part, a firing button 154 operably connected to the first fire lever 356 and second fire lever 364. The first fire lever 356 extends from a front end to a rear end, and is pivotally connected to the right body 216 by a pivot pin 357. A pin 157 extends from the first fire lever 356 underneath the firing button 154. The first end of the first fire lever 356 forms a counter pusher 358 extending forward, through an opening 259 in the front plate 256, toward the extension arm opening 359, and terminating in a tip 361. The tip 361 contacts the end of the extension arm 132 extending into the first end 200 of the actuator 152 housing, whereby downward movement of the front end of the first fire lever 356 moves the advancement member 124 into engagement with the first number wheel 104.

A first fire lever spring 360 at the rear of the first fire lever 356 extends from a first end within a notch of the lever 356 rearward to a second end in contact with the interior of the right body 216. The spring pushes the rear end of the first fire lever 356 downward, rotating the first fire lever 356 about the pivot pin 357, urging the rear end toward the bottom of the actuator 152. When the needle carrier 278 is in the fired position, the rear end of the first fire lever 356 is at the top surface of the needle carrier 278. Upon arming the needle carrier 278, the rear end of the first fire lever 356 passes over the front edge of the needle carrier 278 causing the first fire lever spring 360 to move the rear end of the first fire lever 356 into contact with the front of the needle carrier 278 thereby preventing forward movement of the needle carrier 278 in response to the biasing force of the compressed spring 288.

The second fire lever 364 extends from a front end to a rear end, and is pivotally connected to the left body 206 by a pivot pin 365. A pin 159 extends from the second fire lever 364 underneath the firing button 154. A second fire lever spring 366 at the rear of the second fire lever 364 extends from a first end within a notch of the lever 364 rearward to a second end in contact with the interior of the left body 206. The spring pushes the rear end of the second fire lever 370 downward, rotating the second fire lever 364 about the pivot pin 365, urging the rear end toward the bottom of the actuator 152. When the cannula carrier 260 is in the fired position, the rear end of the second fire lever 364 is at the top surface of the cannula carrier 260. Upon arming the cannula carrier 260, the rear end of the second fire lever 364 passes over the front edge of the cannula carrier 260 causing the second fire lever spring 266 to move the rear end of the second fire lever 364 into contact with the front of the cannula carrier 260 thereby preventing forward movement of the cannula carrier 260 in response to the biasing force of the compressed spring 272. Arming of the cannula carrier 260 pivots the second fire lever 364 about the pivot pin 365 raising the firing button 154 upward.

A safety assembly prevents the firing button 154 from being depressed once the actuator 152 is armed. Disengaging the safety assembly allows the needle assembly 158 to be fired. The safety assembly includes a lever safety 340 guiding a safety switch 342. The lever safety 340 is mounted to the lever carrier shaft 292, and forms an upwardly open channel slideably receiving the safety switch 342. The safety switch 342 has a body forming a rail extending from a front end to a rear end. The rail moves within the upwardly open channel. The rear end forms a neck extending upward to the body forming a button 346 accessible from the exterior of the housing 166. The front end of the switch 342 contacts a spring biasing the switch 342 rearward. Referring to FIG. 18, the switch 342 is in an engaged position to prevent downward movement of the firing button 154. A notch between the front end and the button 346 allows the firing button 154 to move downward when the safety switch is in a firing position. The safety switch 342 forms fins 348 extending laterally from the neck between the second end and the button 346. The fins 348 form a top surface with a front and rear top surface that each slope downward from a peak. The fins 348 engage detents in the interior surfaces of the left and right bodies 206, 216. When the safety assembly is engaged, the button 346 is in a rearward position, and the body of the switch 342 is beneath the firing button 153 preventing downward movement of the firing button 153. To disengage the safety assembly a user presses downward on the button 346, moving the fins 348 downward out of engagement with the body detents, while pushing the button 346 forward toward the firing button 154. Moving the button 346 forward moves the notch between the front end and the button 346 to a position below the firing button 154 allowing the firing button 154 to move downward.

The needle carrier 278 and cannula carrier 260 are sequentially fired by depressing the firing button 154. Moving the firing button 154 downward moves the first fire lever 356, through the pin 157, rotating the first fire lever 356 about the pivot pin 357, and moves the second fire lever 364 through the pin 59, rotating the second fire lever 364 about the pivot pin 365, elevating the rear end of the first fire lever 356 and disengaging the rear end from contact with the needle carrier 278, and elevating the rear end of the second fire lever 364 and disengaging the rear end from contact with the cannula carrier 260. If an event counter 100 is attached to the front of the actuator 152, depressing the firing button 154 moves the front end of the counter pusher 258 downward, from a first position to a second position, into contact with the extension arm 132, causing the first number wheel 104 to advance one digit thereby registering a firing of the actuator 152. The cannula carrier 260 remains stationary momentarily as the needle carrier 278 moves forward from an armed position to a fired position. The spring 288 decompresses, releasing its stored energy, and quickly moves the needle carrier 278 forward driving the tip 187 of the needle 188 forward until forward movement of the carrier is stopped by the front of the needle carrier 278 contacting the stop plate 316. When the needle carrier 278 is in the fired position and the cannula carrier 260 is in an armed position the core bed 190 of the needle 188 is exposed, and when fired into a target tissue 186, the core bed 190 fills with tissue (FIG. 26). In an embodiment, the distance between the front surface of the needle carrier 278 in the armed position and the rear surface 323 of the stop plate 316 determines the length of the core bed 190 exposed to the target tissue 186 and the approximate length of the tissue specimen 194 captured by the biopsy needle assembly 158 upon subsequent firing of the cannula 193. Transverse ridges extending across the core bed 190 grip the tissue specimen 194 when the cannula 193 is fired, aiding in retaining the tissue specimen 194 in the core bed 190 and helping to prevent bunching of the tissue specimen 194 adjacent the tip 187 end of the core bed 190. The striking of the needle carrier 278 against the stop plate 316 actuates a cannula trigger 374 that fires the cannula carrier 260, moving the cannula 193.

Forward movement of the cannula carrier 260 is prevented by the second fire lever 364 and a tertiary fire lever 370. The tertiary fire lever 370 is below the second fire lever 364, and extends from a first end pivotally connected to the front plate 256 by a pin 371, and a rear end in contact with the front of the cannula carrier 260. A tertiary fire lever spring 372 at the bottom of the tertiary fire lever 370 forms a bow shape depending from the tertiary fire lever 370 with a first end of the spring 372 at the first end of the lever 370 and extending rearward to a second end terminating in a notch in the underside of the tertiary fire lever 370. The spring 372 biases against the interior of the handle body door 238 urging the second end of the tertiary fire lever in front of the cannula carrier 260 when the cannula carrier 260 is in an armed position.

The cannula trigger 374 is a generally U-shaped member forming a first pivot arm 380 and opposite second pivot arm 382 extending from a base. The trigger 374 nests within the front of the stop plate 316 whereby the terminal end of the first pivot arm 380 is pivotally connected to the stop plate 316 between the guide shaft 258 and guide shaft 276, and the terminal end of the second pivot arm 382 is pivotally connected to the left side of the stop pate 316. A needle carrier contact 376 extends from the first pivot arm 380 rearward through a needle carrier contact aperture 317 formed by the stop plate 316 toward the needle carrier 278. The tip of the needle carrier contact 376 extends from the rear surface of the stop plate 316. A secondary fire lever contact 378 extends rearward from the cannula trigger 374 base toward the cannula carrier 260. As the needle carrier 278 strikes the stop plate 316 the needle carrier contact 376 is urged forward causing the cannula trigger 374 to rotate forward, and the secondary fire lever contact 378 to swing in an arch downward into contact with the top of the tertiary fire lever 370 forcing the tertiary fire lever 370 to rotate downward about pin 371. As the tertiary fire lever 370 pivots downward about the front plate 256, the rear end of the tertiary fire lever 370 moves downward, disengaging the rear end from contact with the cannula carrier 260. The spring 272 decompresses and quickly, releasing its stored energy, and moving the cannula carrier 260 forward from the armed position until forward movement of the carrier is stopped by the front of the cannula carrier 260 contacting the stop plate 316.

Figure 28:
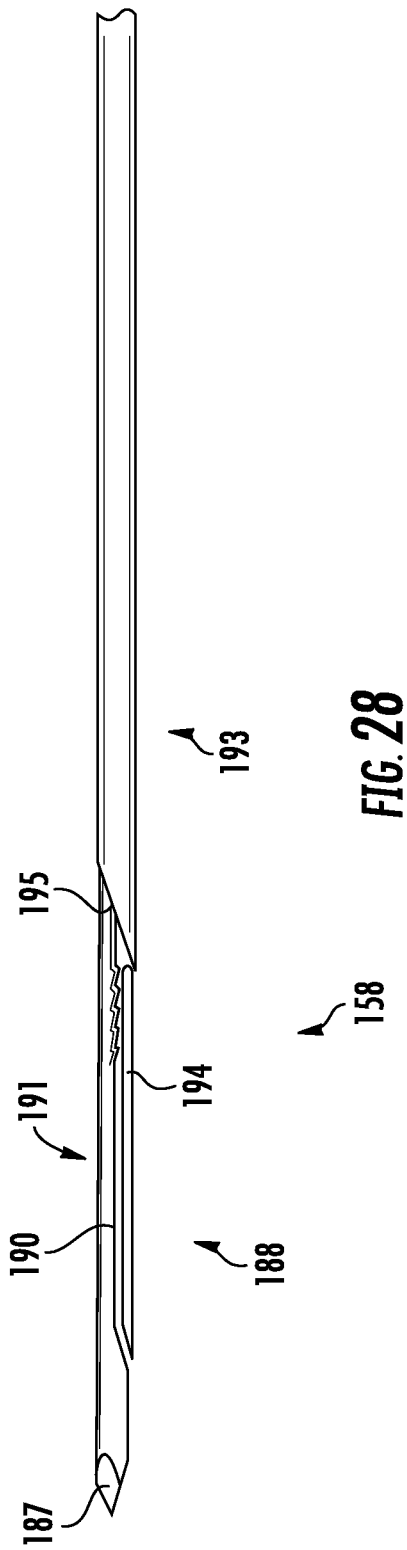
FIG. 28 is an elevation view showing a biopsy needle assembly with the capture tissue specimen exposed.
Figure 29:
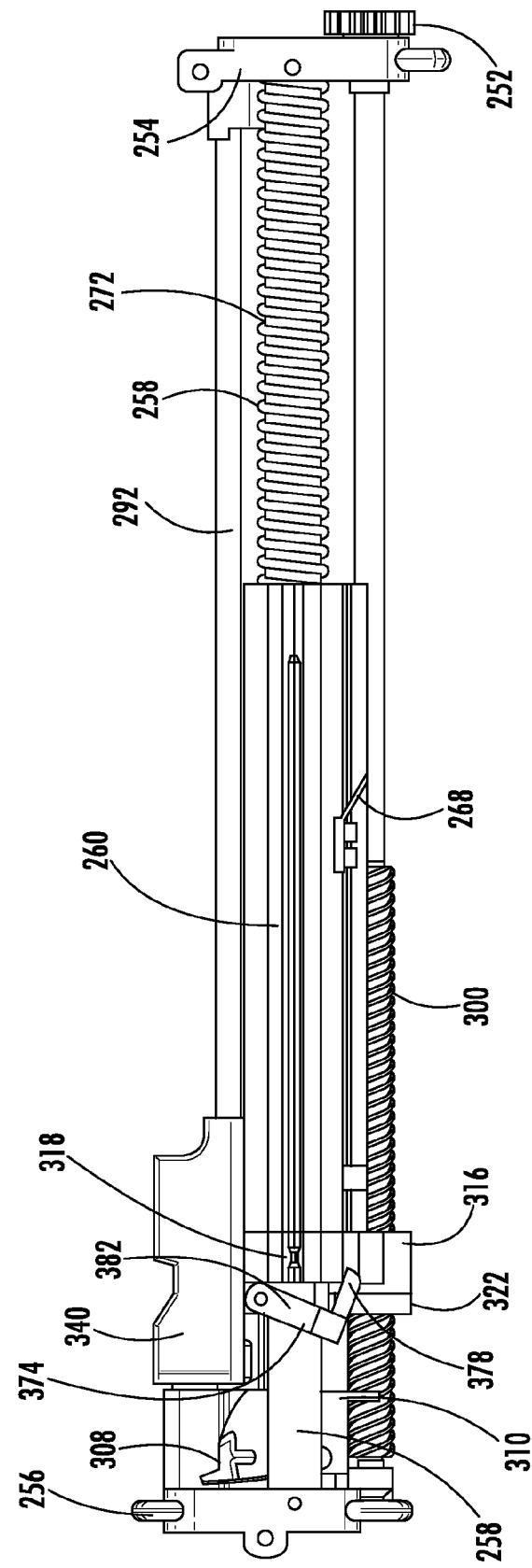
FIG. 29 is an elevation view showing the left side of the actuator with the needle carrier and cannula carrier in a fired condition, and various structural features removed.
Figure 30:
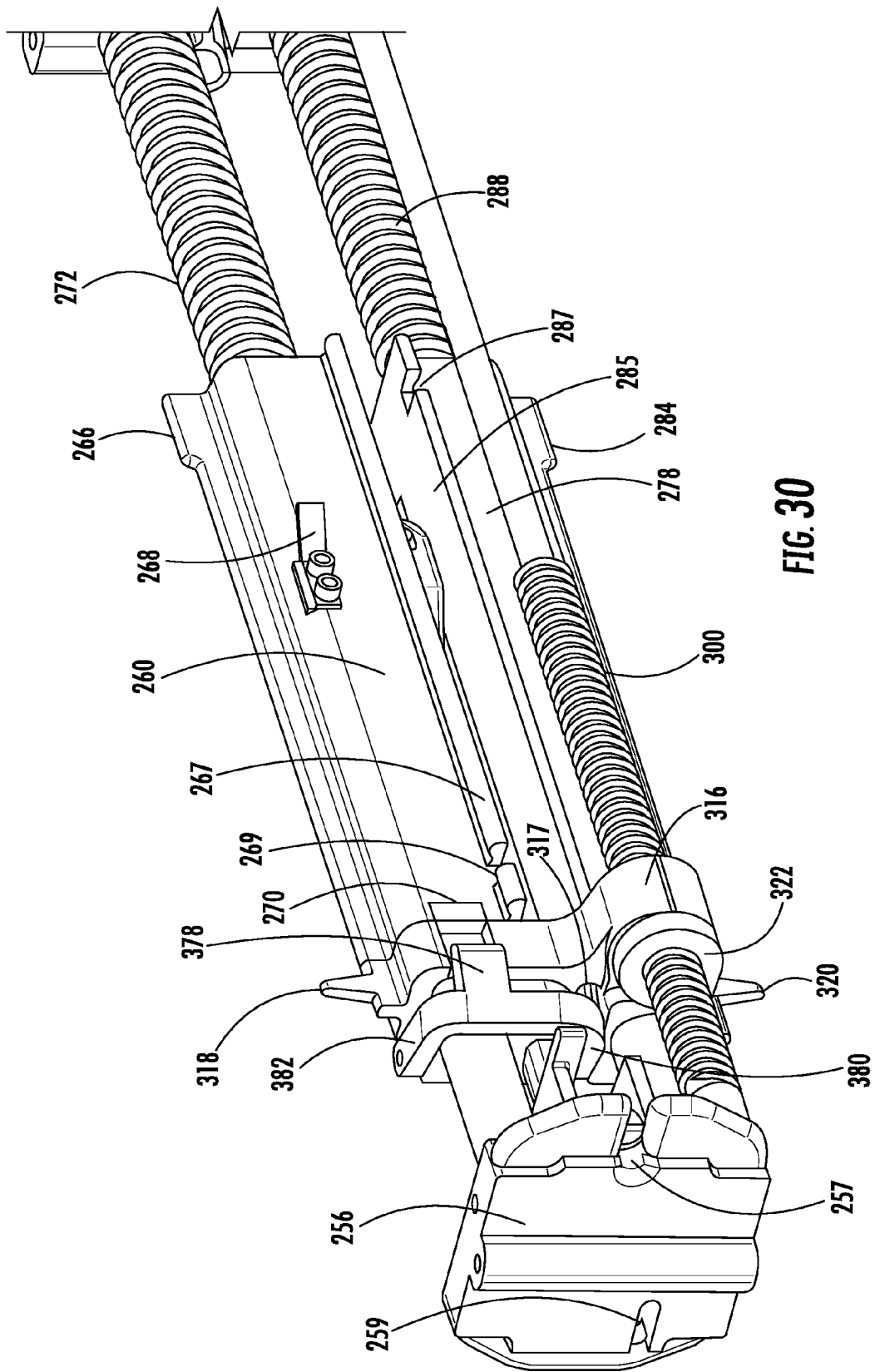
FIG. 30 is an isometric view from the front and below of the actuator shown in FIG. 29.
Figure 31:
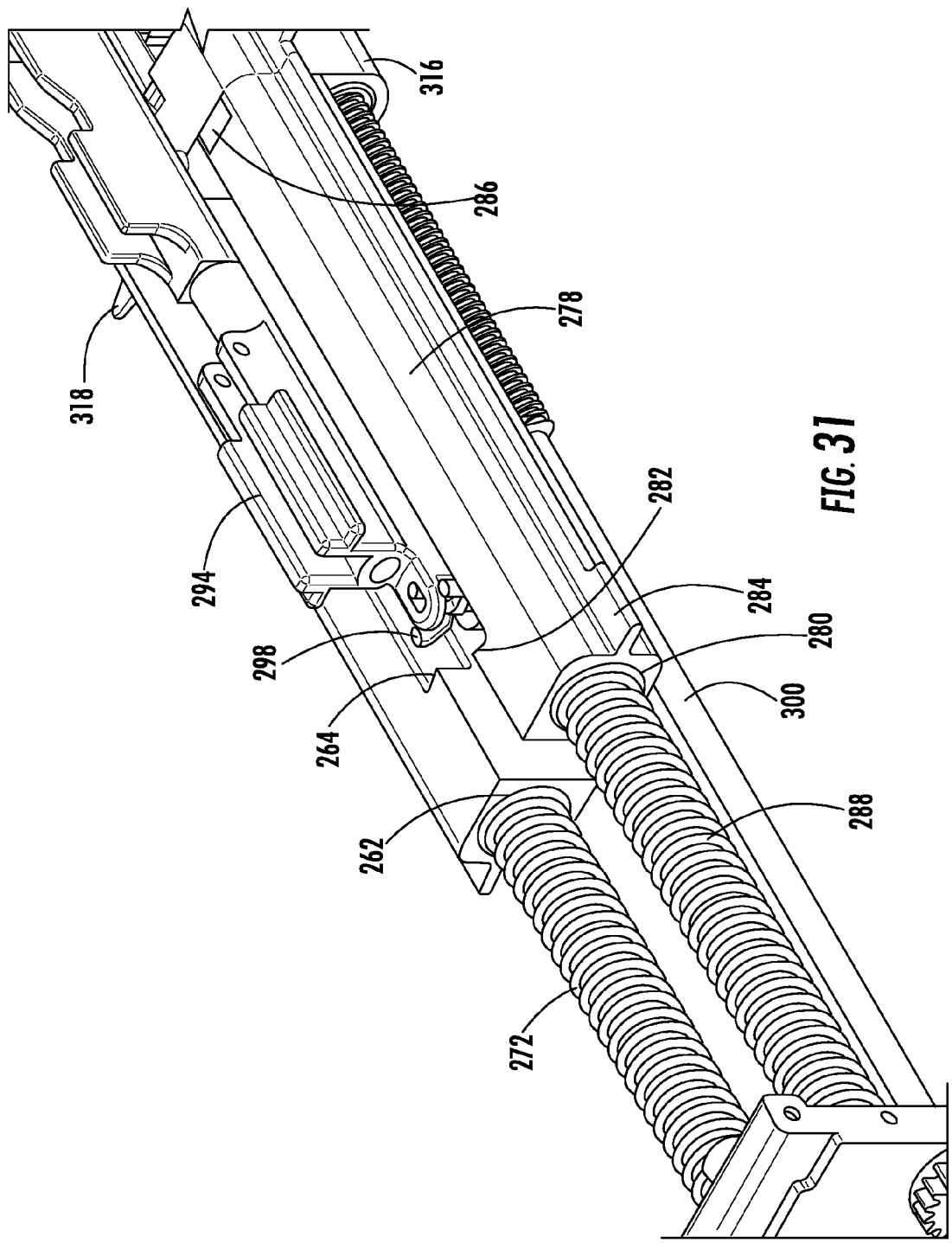
FIG. 31 is an isometric view from the rear and above of the actuator shown in FIG. 29.
Figure 32:
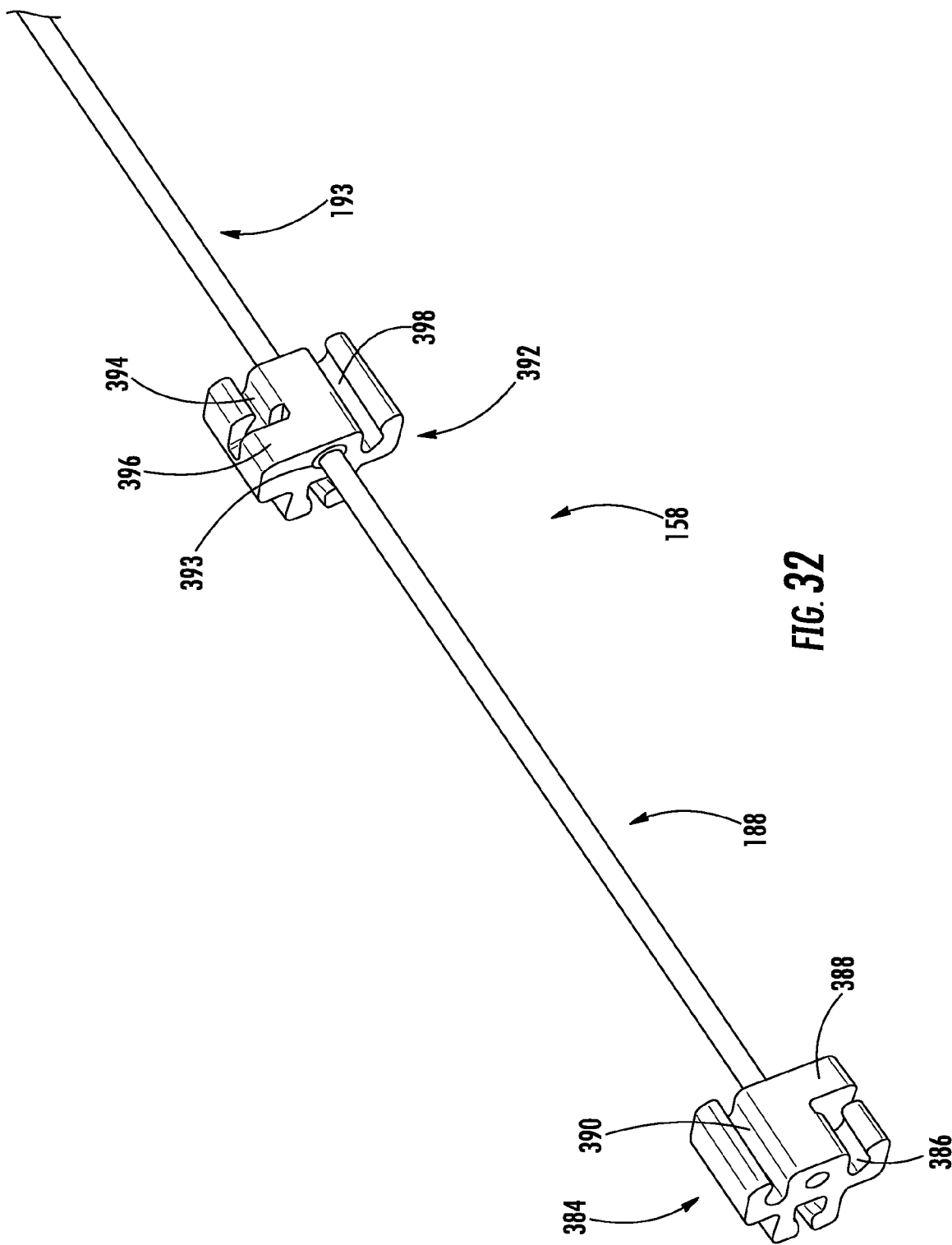
FIG. 32 is an isometric view from the rear of an embodiment of the biopsy needle assembly.
Figure 33:
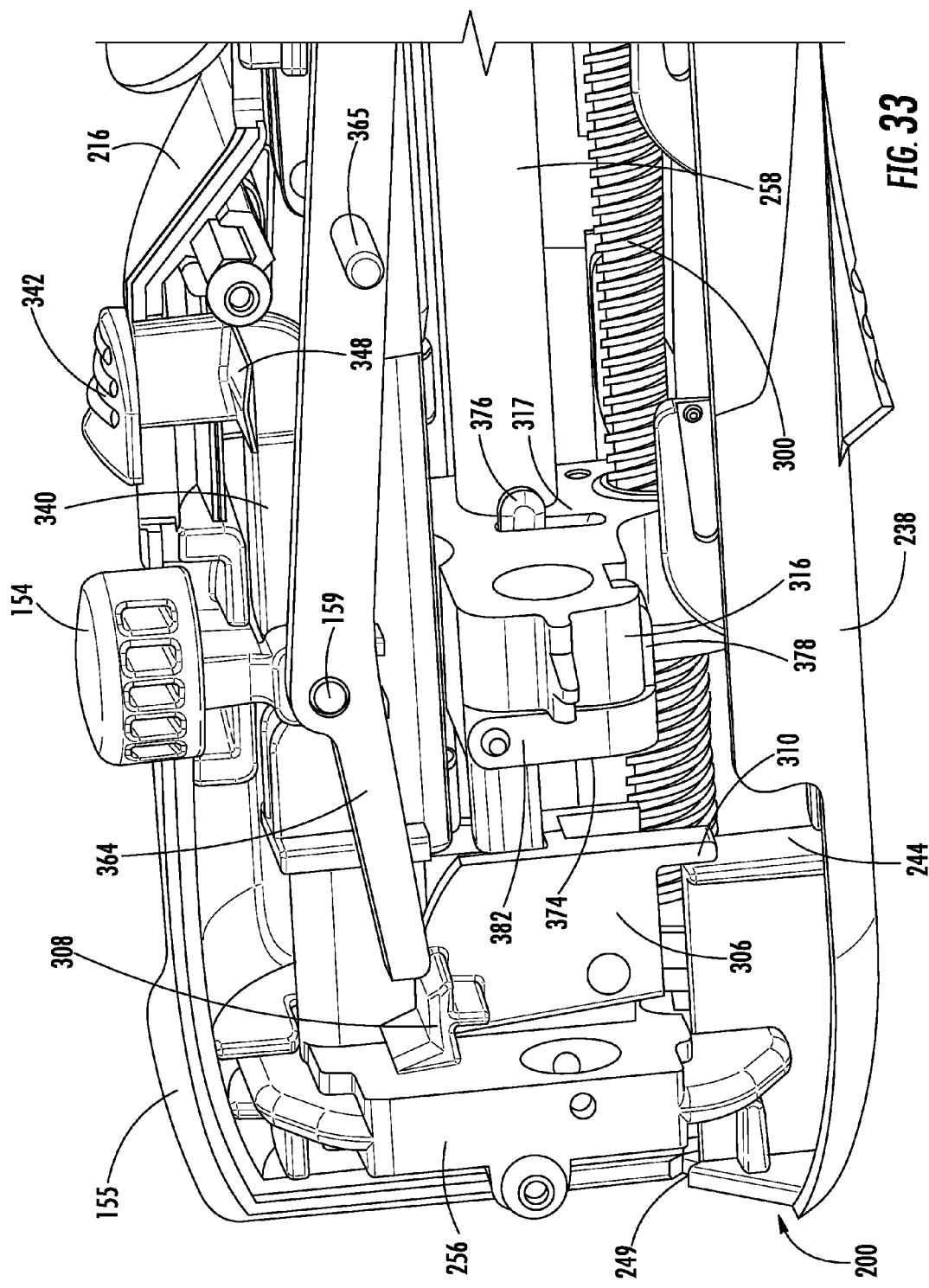
FIG. 33 is an isometric view of the left side of the actuator with the left body removed showing the handle body door safety engagement member engaging the door safety.

As the cannula carrier 260 moves forward when the core bed 190 is filled with tissue, the forward cutting edge 195 of the cannula 193 cuts the tissue within the core bed 190 from the target tissue 186 capturing a tissue specimen 194 between the core bed 190 and cannula 193 (FIG. 27). When the needle carrier 278 is in the fired position and the cannula carrier 260 is in an armed position the core bed 190 of the needle 188 is exposed, and when fired into a target tissue, the core bed 190 fills with tissue. When the cannula carrier 260 and needle carrier 278 are in a fired position (FIG. 27) the biopsy needle assembly 158 can be withdrawn from the target tissue 186 and the tissue specimen 194 can be removed from the core bed 190 by actuating the loading lever 230, retracting the cannula 193, and exposing the core bed 190 (FIG. 28).

Needle assemblies 158 are installed in the actuator 152 by opening the handle body door 238. The rear end of the handle body door 238 forms a door hinge 246. The door hinge 246 forms an elongated slot or door hinge aperture 248. A door hinge pin 242 extends between the left and right sides of the door hinge insert 240 passing through the door hinge aperture 248. The door hinge aperture 248 extends forward and rearward allowing the handle body door 238 to be slid forward, from a locked position to an unlocked position, disengaging tabs with slots at the upper edge of the left and right side of the door 238 from complimentary elements at the lower left edge of the left body 296 and at the lower right edge of the right body 216. The front end of the handle body door 238 forms an upending front wall. The upper edge of the front wall forms a needle passage 249 aligning with an aperture 257 in the front plate 256 allowing the needle assembly 158 to exit the actuator 152. The front end of the door 238 forms a door safety engagement member 244. When the door 238 is in the locked position the engagement member 244 contacts a lower tab 310 of a door safety 306. The door safety 306 forms the lower tab 310 at the rear of a bottom edge, upper tabs 308 extending from the front of a top edge, and is pivotally connected to the front plate 256. When the door is in the locked position, the engagement member 244 urges the lower tab 310 rearward positioning the upper tabs 308 forward of the first fire lever 356 and second fire lever 364 allowing the levers to move downward when the carriers are in the armed position. The door safety 306 is biased by a spring to rotate the safety 306 about the front plate 256 whereby the lower tab 310 moves forward and the upper tabs 308 move rearward. Moving the door 238 forward to an unlocked position allows the lower tab 310 to rotate forward, moving the upper tabs 308 rearward and positioning them beneath the first end of the first and second fire levers 356, 364, thereby preventing downward movement of the levers 356, 364 and the firing of the carriers 260, 278. After sliding the door 238 forward, the bottom of the actuator 152 is accessed by moving the front of the door 238 downward, allowing servicing of the actuator 152 or the loading or unloading of a biopsy needle assembly 158.

Referring to FIGS. 25-28, and 32, an embodiment of the biopsy needle assembly 158 is shown. The needle 188 includes a needle hub 384 for connecting the needle 188 to the needle carrier 278, and the cannula 193 includes a cannula hub 392 for connecting the cannula 193 to the cannula carrier 260. The needle carrier 278 forms a needle carrier ridge 285 depending therefrom toward the bottom of the actuator 152, and the cannula carrier 260 forms a cannula carrier ridge 267 depending therefrom toward the bottom of the actuator 152.

The needle hub 384 is at the rear of the needle 188 and forms a needle ridge guide 386 and an adjacent cannula ridge guide 390. A needle hub tab 388 engages a needle ridge slot 287 in the needle ridge 285 at the rear end of the needle ridge 285, whereby movement of the needle carrier 278 moves the needle 188. The cannula ridge 267 is slideably received by the cannula ridge guide 390, aiding in alignment of the needle 188 within the cannula 193, and aiding in alignment of the biopsy needle assembly 158 as it exits the front of the housing 166.

The cannula hub 392 is at the rear of the cannula 193 and forms a passage 393 communicating with the interior of the cannula 193 allowing the needle 188 to be slideably received within the cannula 192. The cannula hub 392 further forms a cannula ridge guide 394 and an adjacent needle ridge guide 398. A cannula hub tab 396 engages a cannula ridge slot 269 in the cannula ridge 267 at the front end of the cannula ridge 267, whereby movement of the cannula carrier 260 move the cannula 192. The needle ridge 398 is slideably received by the needle ridge guide 398, aiding in alignment of the cannula 193 and the biopsy needle assembly 158 as it exits the front of the housing 166.

Actuators 152 using event counters 100 can be used in conjunction with gridded aperture guides and a biopsy specimen carrier system as indicated above, to provide a numerical link between the guide or step in the procedure, the biopsy specimen excised using the actuator 152, and biopsy specimen receptacles of a biopsy specimen carrier system increasing the accuracy of the biopsy data acquired during the procedure, and reducing the mix-up of biopsy specimens.

Traditionally, biopsies are taken with the core bed of the biopsy needle facing upward. In an embodiment, biopsy needle assemblies 158 are loaded into the biopsy needle actuator 152 whereby the orientation of the core bed 190 in the needle 188 is downward or in the six o'clock position relative to the actuator 152 when the needle assembly 158 is used to excise a biopsy tissue specimen 194 (FIGS. 25-28). Further, a sight 155, such as a marking, bump, or rib is formed at a first side or top of the housing 101, such as adjacent the firing button 154. In an embodiment, the needle assembly 158 is mounted within the actuator 152 whereby the core bed 190 is oriented to face one hundred eighty degrees from the sight 155 whereby the core bed 190 is facing in a downward orientation. The sight 155 provides an indication to the user that the core bed 190 is orientated downward. Orientating the core bed 190 downward orientates the excised tissue specimen on the underside of the needle assembly 158. Therefore, after the biopsy needle assembly 158 is fired by the actuator 152 and the excised tissue specimen 194 is taken from the target tissue, upon retraction of the cannula 192 to expose the specimen 194, transfer of the specimen 194 to a biopsy specimen receptacle is expedited because the user does not need to rotate the actuator 152 in their hand to properly orientate the specimen 194 before transferring the specimen 194 to the receptacle.

The various components of the counter 100, actuator 152, and biopsy needle assembly 158 are manufactured from polymer materials, metallic materials, or otherwise from materials that can withstand repeated heat, steam, and chemical sterilization. Metallic materials include stainless steel, and cobalt chrome. Polymer materials include RADEL® R-500 manufactured by Solvay Specialty Polymers USA, LLC of Alpharetta, Ga.

As required, detailed aspects of the present disclosed subject matter are disclosed herein; however, it is to be understood that the disclosed aspects are merely exemplary of the disclosed subject matter, which may be embodied in various forms. Therefore, specific structural and functional details disclosed herein are not to be interpreted as limiting, but merely as a basis for the claims and as a representative basis for teaching one skilled in the art to variously employ the present disclosed subject matter in virtually any appropriately detailed structure.

Although the subject matter has been disclosed with reference to various particular embodiments, it is understood that equivalents may be employed and substitutions made herein without departing from the scope of the disclosed subject matter.

Having described the disclosed subject matter, what is claimed as new and desired to be secured by Letters Patent is:

1. A biopsy device, comprising:
   a biopsy needle actuator within a housing, the biopsy needle actuator, comprising:
   a cannula carrier guide shaft adjacent a needle carrier guide shaft;
   a cannula carrier with a front surface, the cannula carrier forming a tubular passage, wherein the cannula carrier guide shaft is slideably received within the cannula carrier tubular passage;
   a needle carrier with a front surface, the needle carrier forming a tubular passage, wherein the needle carrier guide shaft is slideably received within the needle carrier tubular passage;
   a stop plate, comprising:
   a rear surface, wherein the stop plate rear surface faces the carrier front surfaces;
   a tab extending from the stop plate toward the housing forming an indicator visible within a distance window framed by the housing;
   a lead screw threadably received by the stop plate; and wherein rotation of the lead screw moves the stop plate on the cannula carrier guide shaft and needle carrier guide shaft;

a lifecycle indicator, comprising:
an indicator wheel presenting a first field and a second field;
wherein the housing forms a lifecycle indicator window framing the indicator wheel; and
wherein the movement of the cannula carrier toward the cannula carrier guide shaft second end selectively rotates the indicator wheel.

2. The biopsy device of claim 1, wherein the distance between the stop plate rear surface and the carrier front surfaces is adjustable between about 20 mm to about 60 mm.

3. The biopsy device of claim 1, further comprising:
wherein the cannula carrier extends from a front end to a rear end, and the front end forms the front surface; and
a fin extending from the rear end of the cannula carrier toward the housing forming an indicator visible within an indicator window framed by the housing.

4. The biopsy device of claim 1, further comprising:
a sight formed at a first side of the housing;
a needle forming a notch with a core bed, wherein the needle is operably connected to the needle carrier; and
wherein the core bed is orientated facing one hundred eighty degrees from the first side of the housing.

5. The biopsy device of claim 4, wherein the core bed forms transverse ridges.

6. A biopsy device, comprising:
a housing;
a biopsy needle actuator within the housing, comprising:
a cannula carrier guide shaft extending between a first end and a second end;
a needle carrier guide shaft extending between a first end and a second end;
a cannula carrier forming a tubular passage extending from a front end to a rear end, the cannula carrier guide shaft slideably received within the cannula carrier tubular passage, and wherein the cannula carrier is moveable between the guide shaft first end and second end;
a needle carrier forming a tubular passage extending from a front end to a rear end, the needle carrier guide shaft slideably received within the needle carrier tubular passage, and wherein the needle carrier is moveable between the guide shaft first end and second end;
a stop plate slideably received on the cannula carrier guide shaft and needle carrier guide shaft; and
a lead screw threadably received by the stop plate, wherein rotation of the lead screw moves the stop plate between the guide shaft first ends and the carriers;
a lifecycle indicator comprising an indicator wheel rotated upon movement of the cannula carrier to the cannula carrier guide shaft second end;
an event counter comprising a first number wheel rotated upon movement of a firing button;
a sight formed on the housing the top of the housing;
a needle forming a notch with a core bed, wherein the needle is operably connected to the needle carrier; and
wherein the core bed is orientated facing one hundred eighty degrees from the first side of the housing.

7. The stop plate of claim 6, further comprising:
a tab extending from the stop plate toward the housing forming an indicator visible within a distance window framed by the housing.

8. A biopsy device, comprising:
a housing;
a biopsy needle actuator within the housing, comprising:
a needle carrier guide shaft extending between a first end and a second end;
a needle carrier forming a tubular passage extending from a front end to a rear end, the needle carrier guide shaft slideably received within the needle carrier tubular passage, and wherein the needle carrier is moveable between the guide shaft first end and second end;
a stop plate slideably received on the needle carrier guide shaft; and
a lead screw threadably received by the stop plate, wherein rotation of the lead screw moves the stop plate between the needle carrier guide shaft first end and the needle carrier front end;
a lifecycle indicator, comprising:
an indicator wheel presenting a first field and a second field;
wherein the housing forms a lifecycle indicator window framing the indicator wheel; and
wherein the movement of the cannula carrier toward the cannula carrier guide shaft second end selectively rotates the indicator wheel.

9. The biopsy device of claim 8, further comprising:
an event counter; and
wherein the event counter registers movement of a firing button.

10. The biopsy device of claim 8, further comprising:
a cannula carrier guide shaft extending between a first end and a second end, the cannula carrier guide shaft disposed adjacent the needle carrier guide shaft;
a cannula carrier forming a tubular passage extending from a front end to a rear end, the cannula carrier guide shaft slideably received within the cannula carrier tubular passage, and wherein the cannula carrier is moveable between the guide shaft first end and second end;
a lifecycle indicator registering movement of the cannula carrier toward the cannula carrier guide shaft second end.

11. The biopsy device of claim 8, further comprising:
a needle forming a notch with a core bed;
wherein the core bed forms transverse ridges; and
wherein the needle is operably connected to the needle carrier.

12. The stop plate of claim 8, further comprising a tab extending from the stop plate toward the housing forming an indicator visible within a distance window framed by the housing.

13. The biopsy device of claim 1, further comprising:
an event counter, comprising:
a frame forming a first side and opposite second side;
a first number wheel adjacent a second number wheel rotatable within the frame;
the first number wheel forming teeth; and
an advancement member for rotating the first number wheel, comprising:
a pawl connected to an extension arm, wherein the pawl engages the first number wheel teeth;
a guide, comprising:
a channel forming a front portion connected to a rear portion;
the front portion and the rear portion extending between a first end and a second end; and the front and rear portions forming an angular inner wall; and
    wherein the pawl is guided into engagement with the first number wheel teeth by the front portion of the guide; and
wherein firing of the biopsy needle actuator moves the extension arm thereby engaging the pawl with the first number wheel.

14. The biopsy device of claim 13, wherein the event counter guide is formed by the frame first side.

15. The biopsy device of claim 13, wherein:
the event counter advancement member forms a pin extending into the channel; and
wherein movement of the pin within the front portion from the first end to the second end engages the pawl with the first number wheel teeth.

16. The biopsy device of claim 13, wherein:
the event counter inner wall of the front portion transitions from the first end to the second end extending laterally from the first end; and
wherein the second end forms a step transitioning between the front portion and the rear portion.

17. The biopsy device of claim 16, wherein the event counter inner wall of the front portion transitions from the first end toward the first number wheel.

18. The biopsy device of claim 13, wherein the event counter inner wall of the rear portion transitions from the second end to the first end extending laterally from the second end.

19. The biopsy device of claim 18, wherein the event counter inner wall of the rear portion transitions from the second end toward the first number wheel.

20. The biopsy device of claim 1, further comprising:
the lifecycle indicator, comprising:
    a first gear assembly engaging a second gear assembly;
    a first shaft extending between a first end and a second end, the first gear assembly connected to a the first shaft;
    a second shaft extending between a first end and a second end, the second gear assembly connected to the second shaft;
    a ratchet gear assembly connected to the first shaft, the ratchet gear assembly rotatable in a first direction and in an opposite second direction;
    a pawl member connected to the second shaft, the pawl member engaging the ratchet gear assembly;
    wherein the indicator wheel is at the first shaft second end, a
    a ratchet pusher for rotating the ratchet gear assembly in the first direction; and the pawl member engaging the ratchet gear assembly preventing rotation of the ratchet gear assembly in the second direction.

21. The biopsy device of claim 20, wherein the lifecycle indicator ratchet pusher is connected to the cannula carrier.

22. The biopsy device of claim 20, wherein:
the lifecycle indicator ratchet gear assembly is connected to the first end of the first shaft; and
the pawl member is connected to the first end of the second shaft.

23. The biopsy device of claim 20, wherein:
the lifecycle indicator housing forms a lifecycle indicator window framing a portion of the indicator wheel;
the indicator wheel presents a first field and a second field; and
the fields are selectively visible through the lifecycle indicator window.

24. The biopsy device of claim 20, wherein arming the biopsy needle actuator engages the ratchet pusher with the ratchet gear assembly rotating the ratchet gear assembly in the first direction.

25. The biopsy device of claim 6, wherein the event counter further comprises:
    a frame forming a first side and opposite second side;
    the first number wheel disposed adjacent a second number wheel rotatable within the frame;
    the first number wheel forming teeth;
    an advancement member for rotating the first number wheel, comprising:
        a pawl connected to an extension arm, wherein the pawl engages the first number wheel teeth;
    a guide formed by the frame first side, the guide comprising:
        a channel forming a front portion connected to a rear portion;
        the front portion and the rear portion extending between a first end and a second end; and
        the front and rear portions forming an angular inner wall; and
    wherein the pawl is guided into engagement with the first number wheel teeth by the front portion of the guide.

26. The biopsy device of claim 25, wherein:
the event counter advancement member forms a pin extending into the channel; and
movement of the pin within the front portion from the first end to the second end engages the pawl with the first number wheel teeth.

27. The biopsy device of claim 25, wherein:
the event counter inner wall of the front portion transitions from the first end to the second end extending laterally from the first end; and
the second end forms a step transitioning between the front portion and the rear portion.

28. The biopsy device of claim 25, wherein the event counter inner wall of the rear portion transitions from the second end to the first end extending laterally from the second end.

29. The biopsy device of claim 6, wherein the lifecycle indicator further comprises:
    a first gear assembly engaging a second gear assembly;
    a first shaft extending between a first end and a second end, the first gear assembly connected to a the first shaft;
    a second shaft extending between a first end and a second end, the second gear assembly connected to the second shaft;
    a ratchet gear assembly connected to the first shaft, the ratchet gear assembly rotatable in a first direction and in an opposite second direction;
    a pawl member connected to the second shaft, the pawl member engaging the ratchet gear assembly;
    wherein the indicator wheel is disposed at the first shaft second end, the indicator wheel presenting a first field and a second field;
    a ratchet pusher connected to the cannula carrier for rotating the ratchet gear assembly in the first direction; and
    the pawl member engaging the ratchet gear assembly preventing rotation of the ratchet gear assembly in the second direction.

30. The biopsy device of claim 29, wherein:
the lifecycle indicator ratchet gear assembly is connected to the first end of the first shaft; and the pawl member is connected to the first end of the second shaft.

31. The biopsy device of claim 29, wherein:
the lifecycle indicator housing forms a lifecycle indicator window framing a portion of the indicator wheel;
wherein the indicator wheel presents a first field and a second field; and
wherein the fields are selectively visible through the lifecycle indicator window.

32. The biopsy device of claim 29, wherein arming the biopsy needle actuator engages the ratchet pusher with the ratchet gear assembly rotating the ratchet gear assembly in the first direction.

33. The biopsy device of claim 9, wherein the event counter further includes:
a frame forming a first side and opposite second side;
a first number wheel adjacent a second number wheel rotatable within the frame;
the first number wheel forming teeth;
an advancement member for rotating the first number wheel, comprising:
a pawl connected to an extension arm, wherein the pawl engages the first number wheel teeth;
a guide, comprising:
a channel forming a front portion connected to a rear portion; the front portion and the rear portion extending between a first end and a second end; and
the front and rear portions forming an angular inner wall;
wherein the inner wall of the front portion transitions from the first end to the second end extending laterally from the first end; and
wherein the front portion second end forms a step transitioning between the front portion and rear portion; and
wherein the advancement member forms a pin extending into the channel, and movement of the firing button moves the extension arm resulting in movement of the pin within the front portion from the first end to the second end engaging the pawl with the first number wheel teeth.

* * * * *